United States Patent
Longoria et al.

(10) Patent No.: US 11,123,130 B2
(45) Date of Patent: Sep. 21, 2021

(54) RF TISSUE ABLATION DEVICES AND METHODS OF USING THE SAME

(71) Applicant: Charles Somers Living Trust, McClellan, CA (US)

(72) Inventors: James Longoria, Sacramento, CA (US); Roy Chin, Pleasanton, CA (US)

(73) Assignee: Charles Somers Living Trust, McClellan, CA (US)

( * ) Notice: Subject to any disclaimer, the term of this patent is extended or adjusted under 35 U.S.C. 154(b) by 1175 days.

(21) Appl. No.: 14/775,247

(22) PCT Filed: Mar. 14, 2014

(86) PCT No.: PCT/US2014/029556
§ 371 (c)(1),
(2) Date: Sep. 11, 2015

(87) PCT Pub. No.: WO2014/144943
PCT Pub. Date: Sep. 18, 2014

(65) Prior Publication Data
US 2016/0015448 A1    Jan. 21, 2016

Related U.S. Application Data

(60) Provisional application No. 61/800,534, filed on Mar. 15, 2013.

(51) Int. Cl.
*A61B 18/14*    (2006.01)
*A61B 90/00*    (2016.01)
(Continued)

(52) U.S. Cl.
CPC ...... *A61B 18/1445* (2013.01); *A61B 18/1402* (2013.01); *A61B 18/1482* (2013.01);
(Continued)

(58) Field of Classification Search
CPC ............ A61B 18/1445; A61B 18/1485; A61B 18/1402; A61B 18/1482; A61B 90/03;
(Continued)

(56) References Cited

U.S. PATENT DOCUMENTS 2,011,169 A    8/1935 Charles
6,113,598 A    9/2000 Baker
(Continued)

OTHER PUBLICATIONS

Brutchey et al., Positive Temperature Coefficient of Resistivity in Donor-Doped BaTiO3 Ceramics Derived from Nano-Crystals Synthesized at Low Temperature, Adv. Mater. (2008), 20:1029-1033.

*Primary Examiner* — Michael F Peffley
*Assistant Examiner* — Samantha M Good
(74) *Attorney, Agent, or Firm* — Heisler & Associates

(57) ABSTRACT

RF tissue ablation devices are provided. Aspects of the RF tissue ablation devices include an elongated member having a proximal and distal end, first and second jaws at the distal end, wherein the first and second jaws are configured to apply intra and inter RF energy to tissue disposed between the jaws during use, and a connector at the proximal end for operatively connecting to a RF energy source. Also provided are systems that include an RF tissue ablation device operatively coupled to a RF energy source, as well as kits that include the devices and methods of using the devices in RF tissue ablation applications, including cardiac applications.

13 Claims, 18 Drawing Sheets

(51) Int. Cl.
*A61B 18/00* (2006.01)
*A61B 18/12* (2006.01)

(52) U.S. Cl.
CPC .... *A61B 90/03* (2016.02); *A61B 2018/00059* (2013.01); *A61B 2018/00178* (2013.01); *A61B 2018/00351* (2013.01); *A61B 2018/00363* (2013.01); *A61B 2018/00577* (2013.01); *A61B 2018/00654* (2013.01); *A61B 2018/124* (2013.01); *A61B 2018/145* (2013.01); *A61B 2018/1467* (2013.01); *A61B 2090/032* (2016.02)

(58) Field of Classification Search
CPC .... A61B 2090/032; A61B 2018/00059; A61B 2018/00178; A61B 2018/00351; A61B 2018/00363; A61B 2018/00577; A61B 2018/00654; A61B 2018/124; A61B 2018/145; A61B 2018/1467
See application file for complete search history.

(56) References Cited

U.S. PATENT DOCUMENTS

| | | | |
|---|---|---|---|
| 6,770,072 B1 | 8/2004 | Truckai et al. | |
| 7,169,146 B2 | 1/2007 | Truckai et al. | |
| 7,189,233 B2 | 3/2007 | Truckai et al. | |
| 7,309,849 B2 | 12/2007 | Truckai et al. | |
| 7,381,209 B2 | 6/2008 | Truckai et al. | |
| 7,951,147 B2 | 5/2011 | Privitera et al. | |
| 7,981,113 B2 | 7/2011 | Truckai et al. | |
| 2002/0165531 A1* | 11/2002 | Goble | A61B 18/1445 606/40 |
| 2003/0195513 A1 | 10/2003 | Truckai et al. | |
| 2003/0212444 A1* | 11/2003 | Truckai | A61B 18/1445 607/115 |
| 2005/0033282 A1 | 2/2005 | Hooven | |
| 2005/0072827 A1 | 4/2005 | Mollenauer | |
| 2005/0090815 A1 | 4/2005 | Francischelli et al. | |
| 2005/0096651 A1 | 5/2005 | Truckai et al. | |
| 2006/0217699 A1 | 9/2006 | Wang | |
| 2008/0172052 A1 | 7/2008 | Eder et al. | |
| 2010/0036370 A1 | 2/2010 | Mirel et al. | |
| 2011/0251613 A1* | 10/2011 | Guerra | A61B 17/295 606/52 |
| 2011/0301605 A1* | 12/2011 | Horner | A61B 17/29 606/52 |
| 2011/0306973 A1 | 12/2011 | Cummings et al. | |
| 2012/0022527 A1* | 1/2012 | Woodruff | A61B 18/1445 606/45 |
| 2012/0283734 A1* | 11/2012 | Ourada | A61B 18/1445 606/52 |

* cited by examiner

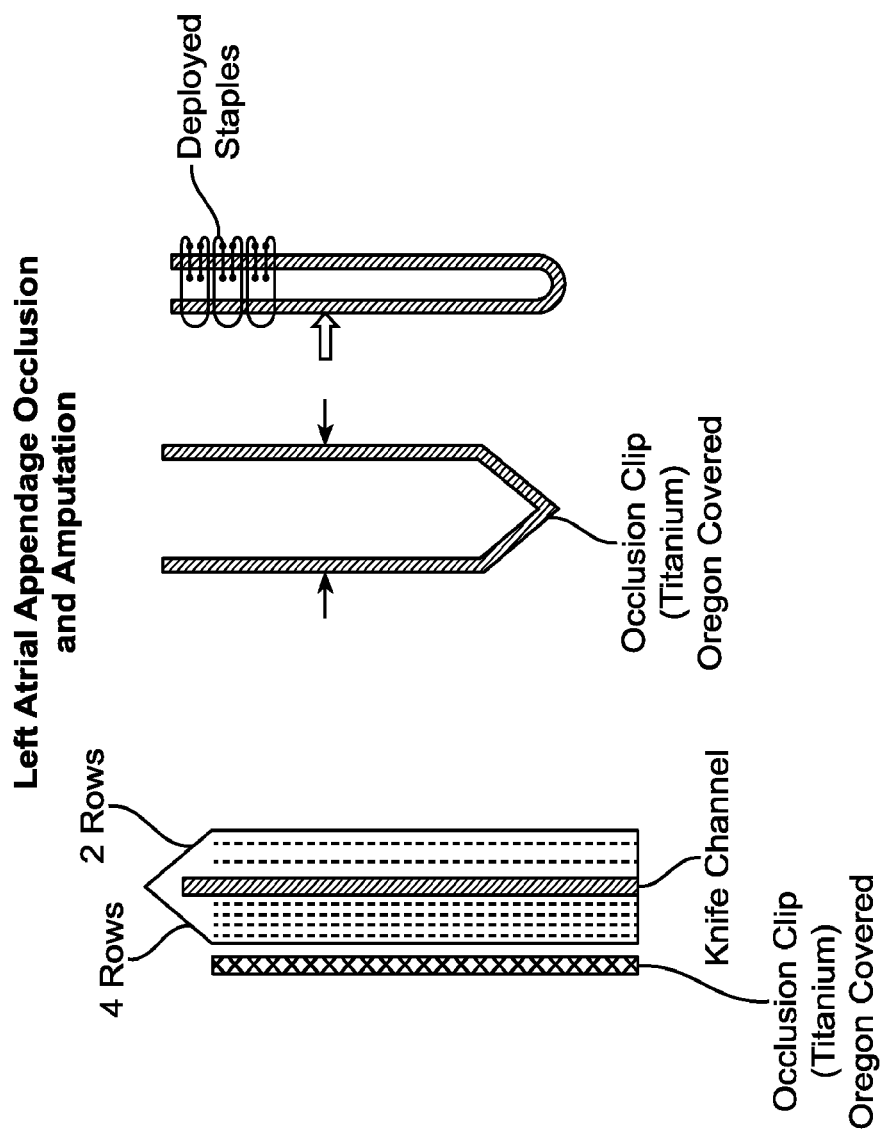

RF TISSUE ABLATION DEVICES AND METHODS OF USING THE SAME

CROSS-REFERENCE TO RELATED APPLICATIONS

Pursuant to 35 U.S.C. § 119 (e), this application claims priority to the filing date of U.S. Provisional Patent Application Ser. No. 61/800,534 filed Mar. 15, 2013; the disclosure of which application is herein incorporated by reference.

INTRODUCTION

Historically, surgery was performed using only mechanical tools, such as mechanical cutting instruments, scalpels, bladed forceps, saws, rongeurs, and the like. However, in recent years, technology has improved such that surgeons now frequently use electromagnetic waves to render a wider variety of surgical effects, e.g., by selectively modifying tissue using electromagnetic energy to produce a specific effect. The characteristics of the electromagnetic energy applied to tissue strongly correlates to the effect that the energy has on the tissue. These characteristics are therefore changed in accordance with the desired tissue effect. One types of electromagnetic energy that is commonly applied during surgery is radiofrequency (RF) electrosurgical energy.

During most medical procedures in which an RF energy source is employed, the RF energy generated for the medical procedure is transferred to a patient via a transmission line. Generally, RF procedures utilize an RF generator, an active electrode and a return electrode. The RF generator generates RF energy typically above 100 kilohertz to avoid muscle and/or nerve stimulation between the active and return electrodes when applied to tissue. During RF procedures, current generated by the RF generator is conducted through the patient's tissue disposed between the two electrodes. The RF energy is returned to the RF source via a return electrode pad positioned under a patient (i.e., a monopolar system configuration) or a smaller return electrode positionable in bodily contact with or immediately adjacent to the surgical site (i.e., a bipolar system configuration). The current causes the tissue to heat up as the electromagnetic wave overcomes the tissue's impedance. Although many other variables affect the total heating of the tissue, usually more current density directly correlates to increased heating.

One example of a medical procedure employing an RF energy source is an RF ablation surgical procedure. RF ablation procedures find use in a variety of therapeutic applications, including cardiac applications (e.g., the treatment of atrial fibrillation), the treatment of hypertension, and the treatment of tumors.

SUMMARY

RF tissue ablation devices are provided. Aspects of the RF tissue ablation devices include an elongated member having a proximal and distal end, first and second jaws at the distal end, wherein the first and second jaws are configured to apply intra and inter RF energy to tissue disposed between the jaws during use, and a connector at the proximal end for operatively connecting to a RF energy source. Also provided are systems that include an RF tissue ablation device operatively coupled to a RF energy source, as well as kits that include the devices and methods of using the devices in RF tissue ablation applications, including cardiac applications.

BRIEF DESCRIPTION OF THE FIGURES

FIGS. 12A and 12B provide details regarding an integrated endoscopic occlusion amputation device, in accordance with an aspect of the invention.

DETAILED DESCRIPTION

Figure 1:
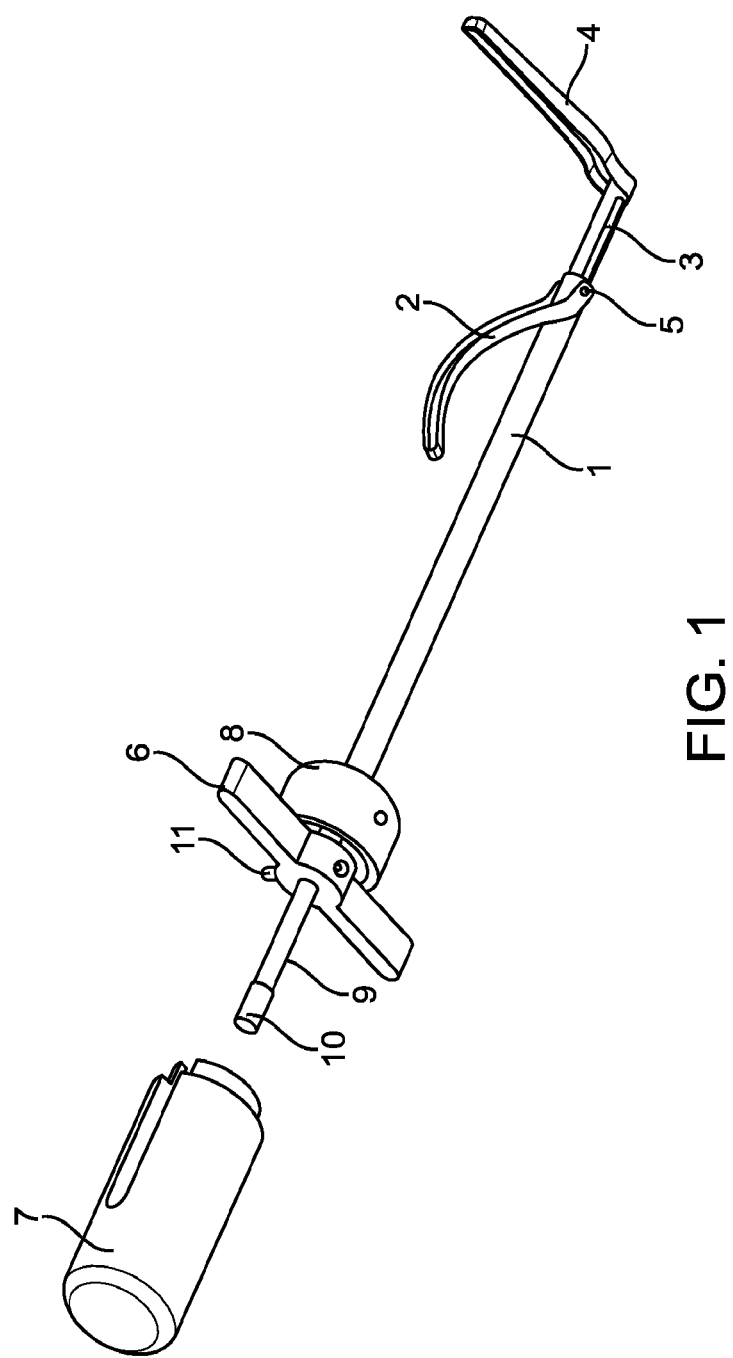
FIG. 1 provides a view of an RF tissue ablation device according to an embodiment of the invention.

RF tissue ablation devices are provided. Aspects of the RF tissue ablation devices include an elongated member having a proximal and distal end, first and second jaws at the distal end, wherein the first and second jaws are configured to apply intra and inter RF energy to tissue disposed between the jaws during use, and a connector at the proximal end for operatively connecting to a RF energy source. Also provided are systems that include an RF tissue ablation device operatively coupled to a RF energy source, as well as kits that include the devices and methods of using the devices in RF tissue ablation applications, including cardiac applications.

Before the methods of the present disclosure are described in greater detail, it is to be understood that the methods of the present disclosure are not limited to particular embodiments described, as such may, of course, vary. It is also to be understood that the terminology used herein is for the purpose of describing particular embodiments only, and is not intended to be limiting, since the scope of the methods of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

Devices

As summarized above, aspects of the invention include RF tissue ablation devices. RF tissue ablation devices are devices configured to apply RF ablative energy to a tissue location of a living organism. By RF ablative energy is meant an alternating current of sufficiently high frequency to ablate target tissue, e.g., by heating the target tissue. The term "ablate" is used in its conventional sense to refer to the removal or destruction of the function of the target tissue. While the frequency employed in a given RF tissue ablation procedure may vary, in some instances the RF ablative energy applied by devices described herein ranges from 250 to 1000 kHz, such as from 300 to 600 kHz, including from 350 to 500 kHz, e.g., from 400 to 500 kHz, at a power level sufficient to raise the target tissue to a sufficiently high temperature for a time sufficient to result in the desired tissue ablation. In some instances, the tissue temperature that is achieved when RF ablative energy is applied to target tissue using the devices described herein is 45° C. or greater, such as 50° C., and in some instances is 105° C. or less, such as 95° C. or less. The devices are configured to apply the RF ablative energy to target tissue for a period of time sufficient to achieve the desired target tissue ablation, and in some instances are configured to apply the RF ablative energy to target tissue for a period of time ranging from 10 to 90 seconds, such as 30 to 60 seconds.

Aspects of the devices include an elongated member having proximal and distal ends, with first and second jaws being positioned at the distal end. While the dimensions of the elongated member may vary widely depending on the particular application for which the device is designed, in some instances the length of the elongated member may range from 1 to 100 cm, such as 5 to 50 cm and including 10 to 35 cm. The cross sectional shape of the elongated member may vary, ranging from circular to oval to rectangular, e.g., square, to triangular, or other convenient shape as desired, where the shape may be the same or different along the length of the elongated member. The longest cross sectional dimension, e.g., outer diameter, of the elongated member may also vary, and in some instances may range from 0.1 to 2 cm, such as 0.5 to 1.5 cm and including 0.75 to 1.25 cm. The elongated member may include one or more internal passageways, e.g., for electrode connectors, e.g., cables, actuator rods for articulated jaws, etc., for operably connecting the distal end elements (e.g., jaws, electrodes, illumination element, etc.) to control elements which may be located at the proximal end.

Positioned at the distal end of the elongated member are first and second jaws, which jaws are configured to apply intra and inter RF energy to tissue disposed between the jaws during use. By "positioned at the distal end" is meant that the first and second jaws are located at least near the distal end of the elongated member, and in some instances within 10 cm or less of the distal end, such as 5 cm or less of the distal. As such, the first and second jaws may be located at the distal end, e.g., where the device has a rongeur configuration, or at least near the actual distal end of the device, e.g., where the device has a clamp configuration.

The first and second jaws are dimensioned to provide for the desired tissue to be positioned therebetween during use in a manner sufficient to achieve the desired tissue ablation. The tissue contact area of the jaws, i.e., that portion of each jaw which is configured to contact tissue during use, may be the same or different. While the tissue contact area of each jaw may vary, in some instances the tissue contact area ranges from 0.1 to 10 cm$^2$, such as 0.5 to 5 cm$^2$. The tissue contact area of each jaw may be planar or non-planar, as desired. Furthermore, the tissue contact area may be smooth or textured, as desired. The jaws may have a length that varies, ranging in some instances from 0.5 to 5 cm, such as 0.75 to 4 cm and including 1 to 2.5 cm. The width of the jaws may also vary, ranging in some instances from 0.1 to 2.5 cm, such as 0.25 to 1 cm and including 0.25 to 0.75 cm.

In some instances, the first and second jaws are configured to apply intra and inter RF energy to tissue disposed between the jaws during use. Intra RF energy is RF energy that does not pass through target tissue disposed between the first and second jaws, while inter RF energy is energy that passes through target tissue disposed between the first and second jaws. In other words, intra RF energy is energy that does not traverse the target tissue, while inter RF energy is energy that traverses the target tissue. Where the target tissue positioned between the first and second jaws during use can be described as being made up of one or more walls, e.g., where target tissue is cardiac tissue clamped between the first and second jaws during a cardiac ablation procedure (such as described in greater detail below), inter RF energy may also be characterized as transmural RF energy, while intra RF energy is non-transmural energy.

In some instances, at least one of the first and second jaws comprises two or more elongated electrodes. The elongate electrodes may span the length of the tissue contact area of each jaw, or just a portion thereof. In some instances, the length of the active area elongated electrodes ranges from 0.5 to 5 cm, such as 0.75 to 4 cm and including 1 to 2.5 cm. The width of the active area of each electrode may also vary, and in some instances ranges from 0.1 to 2.5 cm, such as 0.25 to 1 cm and including 0.25 to 0.75 cm. In some instances, each of the first and second jaws comprises two or more elongated electrodes, such as three, four or five or more elongated electrodes. The number of elongated electrodes on each of the first and second jaws may be the same or different. The configuration of each elongated electrode may also vary, and therefore may be linear, curvilinear, angled, etc., as desired.

Each of the elongated electrodes of the first and second jaws may be made up of any convenient material. Electrode materials of interest include, but are not limited to: platinum group metals, such as platinum, rhodium, palladium, rhenium, as well as tungsten, gold, silver, tantalum, and alloys of these metals; electrically conductive elastic materials, such as nickel/titanium alloys, copper/zinc alloys, or nickel/aluminum alloys; etc.

In some instances, the elongated electrodes include a positive temperature co-efficient of resistivity (PTCR) material, e.g., where the PTCR material may be present as a coating on the active surface of the electrode, or otherwise incorporated into the electrode. PTCR materials of interest include semiconductor materials which exhibit resistivity increases with increasing temperature, specifically an increase that is characterized by a slow increase in resistivity up to a the Curie temperature of the material. When a PTCR material reaches its Curie temperature, its resistivity increases by several orders of magnitude over a very small temperature range. Thus, the amount of current that can flow is very small compared to that which can flow at significantly lower temperatures. After this sharp rise, the resistivity approaches an almost constant value. As such, PTCR materials of interest are those that first undergo a slow increase in resistance as the temperature increases. In the region of their characteristic Curie temperature, their resistivity increases dramatically over a very small temperature range. After this rapid increase, the resistivity approaches a maximum as the temperature rises further. PTCR materials of interest include those having a Curie temperature ranging from 60 to 160° C., such as 75 to 150° C. and including 80 to 125° C. Materials exhibiting PTCR properties include, but are not limited to: semiconducting titanate ceramics, such as but not limited to barium titanate, lead titanate and strontium titanate; ternary perovskites, e.g., $BaTiO_3$, and the like; etc., where these materials may include small amounts of dopants sufficient to provide for the desired semi-conductive property, where dopants of interest include, but are not limited to: trivalent ions (e.g., $Y^{3+}$, $La^{3+}$, $Nd^{3+}$, $Sm^{3+}$, etc.) and the like. Also of interest as PTCR materials are PTC matrix materials, e.g., as described in U.S. Pat. Nos. 7,189,233; 7,196,146; 7,309,849; 7,381,209; and 7,981,113; the disclosures of which are herein incorporated by reference. In brief, such PTC matrix materials are fabricated of a non-conductive polymer e.g., polypropylene or medical grade silicone polymer, that exhibits two phases that define greater and lesser conductive states. The first phase is a crystalline or semi-crystalline state where the polymer molecules form long chains and are arranged in a more ordered architecture. When the temperature of the material is elevated, the polymer molecules maintain the crystalline architecture or structure through a selected temperature range. The polymer is designed to transition to an at least partly amorphous phase from the crystalline state at a selected temperature range. In the amorphous state, the molecules are aligned more randomly, and there may be slight changes in material geometry at the macroscale. The non-conductive polymer is combined with a dispersed, highly conductive particles (e.g., carbon micro- or nanoparticles) to form a matrix. In the crystalline phase of the polymer, the carbon particles are packed into the crystalline boundaries and form many conductive paths across and through the matrix material. In this low temperature crystalline state, the polymer-carbon matrix is engineered to have a low resistance.

As reviewed above, at least one of first and second jaws has at least two elongated electrodes, wherein each of the first and second jaws may include two or more elongated electrodes, e.g., three or more, four or more, five or more, six or more, etc., elongated electrodes. The device may be configured to control the electrodes, e.g., control the polarity of the electrodes, in any desired fashion. For example, the polarity of each of the electrodes may be fixed and not changeable during operation. Alternatively, the device may be configured to independently control the polarity of one or more of the electrodes, including all of the electrodes. For example, the device may be configured to independently control the polarity of each of the electrodes, such that during use the operator may assign the desired polarity to each of the electrodes.

The first and second jaws may assume a variety of different configurations. In some instances, at least one of the first and second jaws is collapsible into the elongated member. By "collapsible into the elongated member" is meant that at least one of the jaws, e.g., the jaw closest to the proximal end, may be folded at least partially into a receiving space, such as a cavity, in the elongated member, for example so that the device has a lower profile during introduction into a body, e.g., prior to deployment and use. In some instances, each of the first and second jaws may be collapsible into the elongated member. Where one or both of the jaws is collapsible into the elongate body, any convenient mechanism may be employed for moving the jaw(s) from the collapsed to deployed state (the latter being employed during application of RF energy to target tissue). For example, one or both of the jaws may be attached to the elongated member via a hinge, and a spring or other force applying mechanism may be employed to assist in transitioning the jaw(s) from the collapsed to deployed state, as desired.

Whether the jaws are collapsible or not, in some instances the first and second jaws are configured to assume a parallel configuration prior to contacting tissue in RF ablative energy engagement, e.g., prior to clamping tissue. As such, prior to tissue engagement, the first and second jaws may be configured to assume a parallel configuration with one another, e.g., where the tissue contact surfaces are in opposing relationship (i.e., facing each other) and the distance between the opposing tissue contact surfaces does not substantially change along the lengths of the electrodes, e.g., where the magnitude of any change is 5 mm or less, such as 2.5 mm or less, including 1 mm or less. In yet other embodiments, the first and second jaws may be configured to assume a non-parallel opposing configuration prior to engaging, e.g., clamping, tissue. In such instances, the distance between the opposing tissue contact surfaces may substantially change along the lengths of the electrodes, e.g., where the magnitude of any chance is 7.5 mm or more, such as 10 mm or more, including 15 mm or more.

In some instances, the first and second jaws are configured to not exceed a compressive force limit on tissue positioned between the jaws during use. In other words, the first and second jaws are configured so that the compressive force applied to tissue engaged by the jaws during application of RF ablative energy does not exceed a predetermined threshold or limit, i.e., compressive force limit. While the compressive force limit may vary, in some instances the compressive force limit is one that does not result in unwanted tissue damage. Any convenient mechanism may be employed to provide for this configuration. In some instances, the device comprises a spring mechanism configured to limit the compressive force applied to tissue positioned between the jaws during use.

Where desired, one of the first and second jaws, such as the jaw most distal from the proximal end of the device, may include an illumination element. Any convenient illumination element may be employed that provides light of one or more wavelengths, such as in the visible range. As such, the illumination element may provide white light or light in a particular wavelength range. The illumination element may vary, where illumination elements of interest include light emitting diodes (LEDs), incandescent bulbs, and the like. The illumination element, when present, may be positioned at any convenient location on the jaw, e.g., at or near the distal end of the jaw (i.e., that end of the jaw furthest away from the elongated member). The illumination element may be configured to be always on during use, or controllable so that it can turned on and off during a procedure, as desired.

As summarized above, in addition to the first and second jaws at the distal end, the RF ablation devices described herein further include a connector at the proximal end for operatively connecting to an RF energy source. Any convenient connection element may be employed. Also present at the proximal end may be one or more actuators, e.g., for deploying the jaw(s), for engaging tissue, for operating the electrodes, for operating the illumination element, for manipulating the distal end of the device, etc.

In some instances, the RF ablation device is configured to be handheld. While the weight of the devices may vary, in some instances the weight of the devices is 3 lbs. or less, such as 2 lbs or less, and including 1 lb. or less, ranging in some instances from 0.25 to 3 lbs, such as 0.50 to 2 lbs.

The RF ablation devices may include a number of additional elements, as desired. For example, the RF ablation devices may include a temperature control element, e.g., cooling element, heat sink, etc., a sensor electrode, a pacing electrode, etc.

Figure 2A:
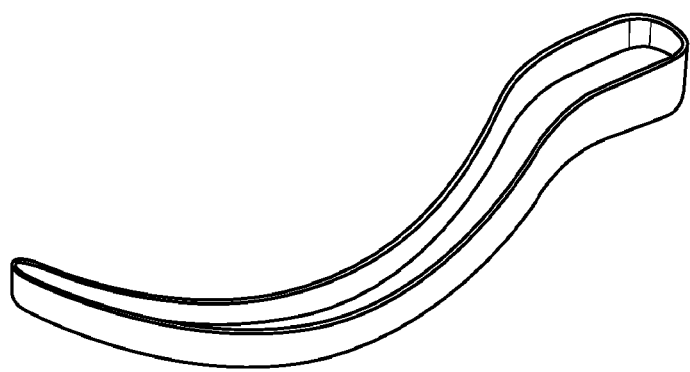
FIGS. 2A and 2B provide views of the distal and proximal jaws, respectively, of the device shown in FIG. 1.
Figure 2B:
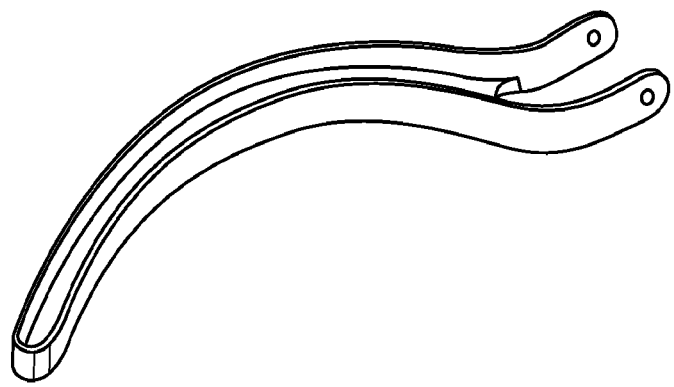
Figure 3A:
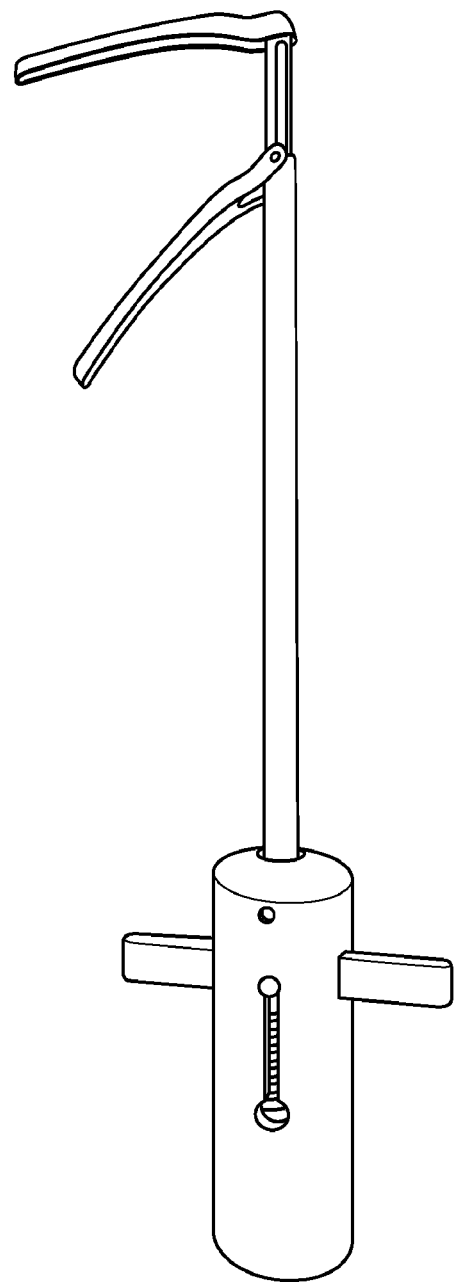
FIGS. 3A and 3B provide views of an RF tissue ablation device according to an embodiment of the invention.
Figure 3B:
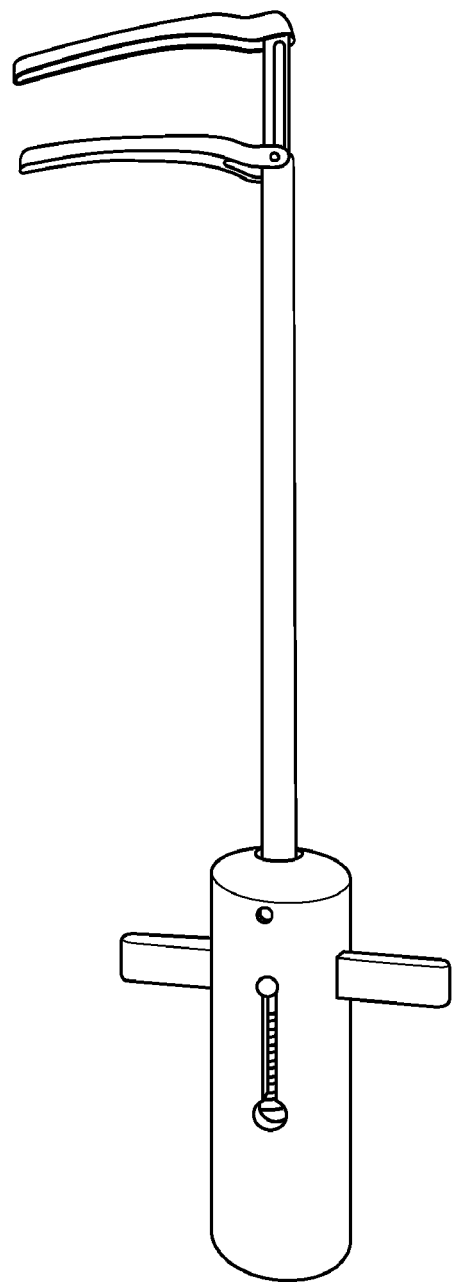

An example of an embodiment of RF ablation device is depicted in FIG. 1. As shown in FIG. 1, the RF ablation device includes elongated member in the form of a tube having a proximal region 1 and a distal region 3. Located at the distal end of distal region 3 is distal jaw 4, which includes three elongated electrodes, not shown. Also shown is proximal jaw 2, which jaw is collapsible onto the elongated member by way of hinge. Proximal jaw 2 also includes three elongated electrodes, not shown. At the proximal end of the proximal region 1 of the elongated member are various control elements, such as proximal pusher 9, distal handle 6 and proximal handle 7. Various adapters are also shown, including proximal handle adaptor 8 and pusher adapter 10. As shown in FIGS. 2A and 2B, the distal and proximal jaws, respectively, have conforming curved profiles. FIGS. 3A and 3B provide views of a clamp device according to embodiments of the invention with the jaws in different configurations.

Figure 4:
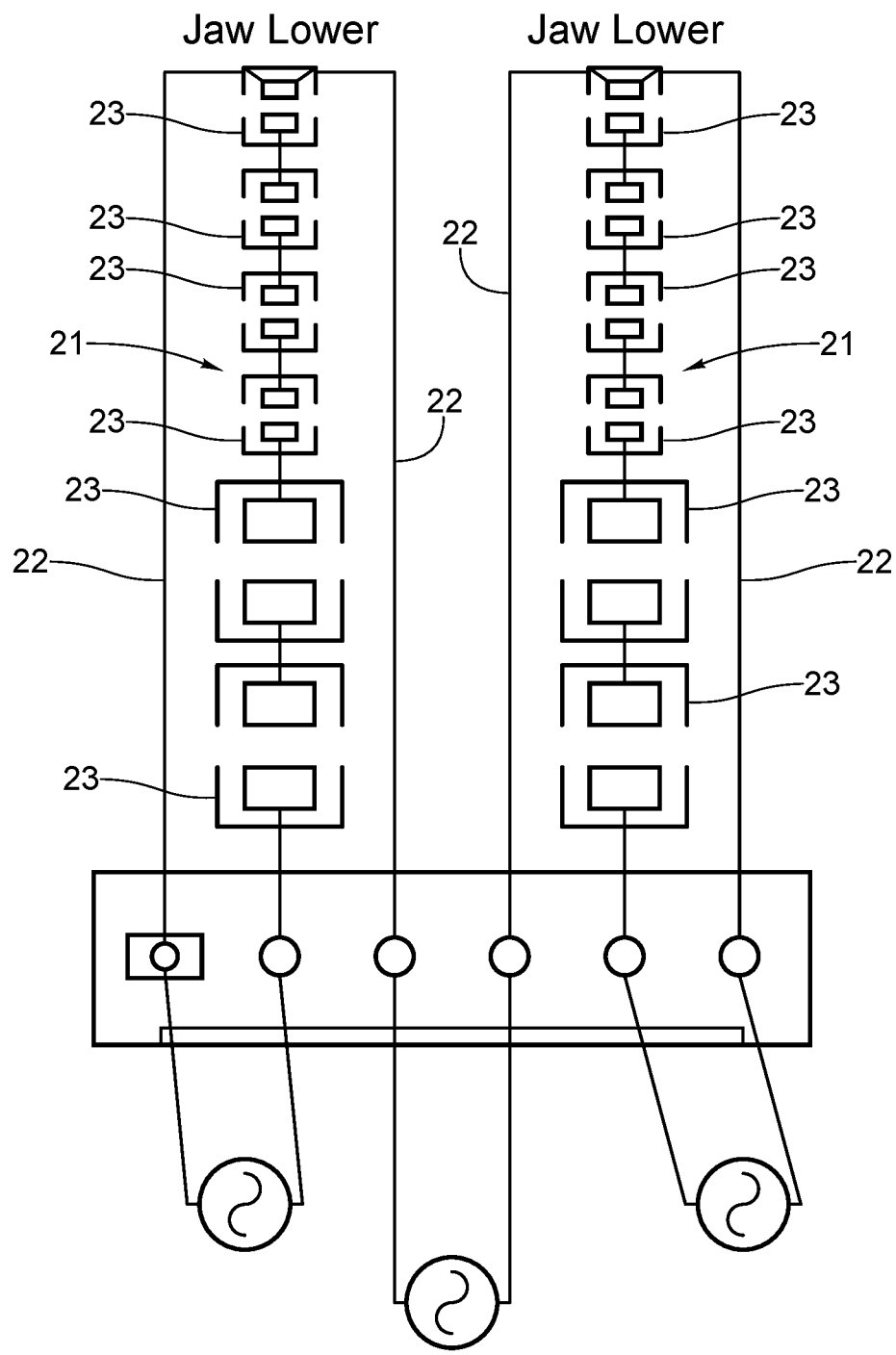
FIG. 4 provides a schematic illustration of the electrode configuration of an inter- and intra-RF ablation device according to an embodiment of the invention.

FIG. 4 provides a schematic illustration of the elongated electrodes and of the proximal and distal jaws as depicted in FIGS. 2A and 2B. 10. As schematically illustrated in FIG. 4, at least one of the first and second jaws, and in this embodiment both of the first and second jaws, includes a central elongated electrode 21 comprising a PTCR material flanked by two non-PTCR material electrodes 22. In other words, each of the proximal and distal jaws includes a central elongated electrode 21 that includes a PTCR material, e.g., as described above, and conventional elongated electrodes 22 on each side of the central electrode 21. In the embodiment shown in FIG. 4, the central elongated electrode 21 includes a plurality of PTCR elements 23 connected in series. While the dimensions of each of the elements 23 may vary, in some instances each element 23 has a surface area ranging from 0.1 to 10, such as 0.5 to 5 and including 0.5 to 2.5 mm$^2$. However, in other embodiments, the central PTCR electrode 21 may include a single elongated PTCR element. Also shown schematically in FIG. 4 is the connection to the RF energy source.

During use, the devices described herein may be operatively connected to an RF energy source. Any convenient RF energy source may be operatively connected to the device, e.g., via the distal end. Examples of suitable energy sources or generators include, but are not limited to, those described in U.S. Pat. Nos. 8,585,694 and 6,235,022.

Methods

Aspects of the methods include ablating tissue with RF tissue ablation devices, e.g., as described above. In general, such methods include positioning target tissue between the first and second jaws and then engaging the tissue with the jaws, e.g., by deploying the jaws into a clamped position about the tissue. As described above, at least one of the first and second jaws may be collapsible relative to the elongated member, e.g., to provide for easier access of the jaws to the target tissue. In such instances, the methods may include positioning the distal end of the elongated member in the vicinity or area of the target tissue and then deploying the collapsed jaw, followed by engagement of the target tissue between the first and second jaws.

Following engagement of the target tissue between the first and second jaws, aspects of the methods include applying intra and inter RF energy to the tissue disposed between the first and second jaws to ablate the tissue, e.g., as described above. Where desired, prior to application of RF energy, the method may include independently selecting the polarity of the electrodes. For example, where each of the first and second jaws includes three electrodes, e.g., as shown in FIG. 4, the methods may include independently selecting the polarity of the central PTCR electrodes so as to provide for transmural ablation of engaged tissue, as well as to provide for intra RF energy to the tissue from the central and flanking electrodes. In a given procedure, RF energy may be applied via the elongated electrodes of the jaws for a desired period of time, where in some instances the period of time ranges from 5 to 120 seconds, such as 15 to 90 seconds, e.g., 30 to 60 seconds. During a given procedure, RF energy may be applied a single time or multiple times in which each time is separated by an intervening period of time in which no RF energy is applied.

As described above, some embodiments of the devices include an illumination element associated with one of the first and second jaws. In such instances, the methods may include detecting light from the illumination element, e.g., by visually detecting the light, detecting the light with a detector, etc. Information from such detection may be employed, as desired, to guide the surgical procedure in which the device is being element, e.g., to guide the correct placement of the distal end of the device in the vicinity of the target tissue, etc.

The target tissue may, in some instances, be part of a living subject or animal. The term "subject" is used interchangeably herein with the term "patient". In certain embodiments, a subject is a "mammal" or a "mammalian" subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" may include human subjects of both genders and at any stage of development (e.g., fetal, neonates, infant, juvenile, adolescent, and adult), where in certain embodiments the human subject is a juvenile, adolescent or adult. While the methods described herein may be applied to perform a cardiac surgical procedure on a human subject, it is to be understood that the subject methods may also be carried out to perform a cardiac surgical procedure on other subjects (that is, on "non-human subjects").

A variety of different target tissues may be ablated with devices as described herein. Types of tissues include, but are not limited to, uterine tissue, vascular structures, e.g., varicose veins, renal arteries, tumors, and cardiac tissue.

In some versions of the disclosed methods, the method is a surgical procedure. As used herein, the phrase "surgical procedure" refers to a procedure (e.g., a medical procedure) involving at least one incision in the body of a subject and/or performed using one or more instruments (e.g., surgical instruments). A surgical procedure may be carried out through a body cavity and/or through the skin of a subject.

As noted above, in certain variations of the disclosed methods, the method is an open surgical procedure. As used herein, the phrase "open surgical procedure" refers to a surgical procedure wherein at least one long incision (e.g., having a length of 10 cm) is made in the body of a subject to introduce at least one surgical instrument and/or visualize the surgery through the incision. In an open surgical procedure, closure devices, e.g., staples, sutures, etc., may be used to close at least one incision.

In certain variations of the disclosed methods, the method is a minimally invasive surgical procedure. As used herein, the phrase "minimally invasive surgical procedure" refers to a surgical procedure that is less invasive than an open surgical procedure. A minimally invasive surgical procedure may involve the use of arthroscopic and/or laparoscopic devices and/or remote-control manipulation of surgical instruments. Minimally invasive surgical procedures include endovascular procedures, which may be totally endovascular procedures, percutaneous endovascular procedures, etc. Endovascular procedures are procedures in which at least a portion of the procedure is carried out using vascular access, e.g., arterial access.

Utility

The devices and methods of the invention, e.g., as described above, find use in a variety of different applications, e.g., applications where ablation of target tissue (such as of a living animal) is desired. Examples of such applications include, but are not limited to, treatment of tumors, e.g., tumors of the liver, treatment of hypertension, e.g., through ablation of renal nerves, treatment of uterine bleeding, and treatment of cardiac conditions, e.g., to treat or prevent atrial fibrillation.

By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

One application of interest in which RF ablation devices described herein find use is in pulmonary vein isolation. The pulmonary veins return oxygenated blood from the lungs to the left atrium. There are typically four pulmonary veins, a superior pulmonary vein and an inferior pulmonary vein from each lung. On the right side of the heart, the superior pulmonary vein passes posterior to the superior vena cava, the inferior behind the right atrium. On the left side of the heart, both the superior and inferior pulmonary veins pass anterior to the descending thoracic aorta.

By "pulmonary vein isolation" is meant a partial or complete electrical isolation of one, two, three, or four pulmonary veins from the left atrium of the heart. Electrical isolation may be achieved using a RF ablative device (e.g., as described herein) to ablate a target tissue of interest. By "ablative" or "ablate" is meant the removal or alteration of electrically-conducting tissue in a target area of interest (e.g., a circumferential ablation region surrounding a pulmonary vein ostium, or two or more (e.g., each) of the four pulmonary vein ostia), such that the tissue no longer conducts or generates an electrical impulse sufficient to generate or propagate an arrhythmia. The process of ablation can prevent an arrhythmia from developing because the tissue that provides a trigger for an arrhythmia has been destroyed. The process of ablation can also prevent an arrhythmia from propagating to other areas of the heart by the creation of a line, or lesion, which electrically isolates the tissue and blocks passage of the electrical impulse. Ablation "lines" or "lesions" can be focal areas which are separate from other areas of ablation, or they can be contiguous, such they form lines or lesions connected to each other, which can form, for example, a continuous line, or ring, or circle, in order to electrically isolate the pulmonary vein(s).

In some embodiments, ablation can be performed by directly contacting a portion of cardiac tissue with an ablative device in a manner sufficient to create a lesion. For example, in some embodiments, an ablation device can be located sufficiently close to an area of cardiac tissue of interest, such that radiofrequency energy is delivered to the cardiac tissue in a manner sufficient to create a lesion. In some embodiments, the ablation is transmural, i.e., extends through the entire heart wall. In other embodiments, the ablation does not extend through the entire thickness of the cardiac wall; however, the degree of ablation may be sufficient to block electrical conduction.

The ablative device may be contacted with a portion of cardiac tissue to form a lesion. The methods can further include repeating the contacting and ablating a number of times to produce a plurality of lesions. For example, the contacting step may be performed two or more times, such as three or more, or four or more times, etc. In some embodiments, the contacting and ablating step is performed in the same location. In some embodiments, the contacting and ablating step can be performed in overlapping locations, such that part of a second location overlaps with part of a first ablating location, such as in the case of creating a continuous linear ablation line. In other embodiments, a second ablation step may be in a different location from the first ablation step, e.g. to create circumferential lesions around the connection area between a pulmonary vein and the left atrium.

As summarized above, the pulmonary vein isolation may be performed using an ablative surgical device, e.g., as described above. An ablative surgical device of the subject methods can be in the shape of a clamp, with an upper and a lower jaw, such that the ablation device is a clamping device. In other embodiments, the ablative device can have an elongated cylindrical shape, such as that of a pen. In some embodiments, the ablation device can have a linear shape, a rectangular shape, a semi-circular shape, an "L" shape, a "U" shape, or any other suitable shape. The configuration of the surface of the ablation device that contacts the tissue can also be any suitable two-dimensional shape such as a line, a square, an oval, a triangle, etc. In some embodiments, the ablation device can further employ suction to pull tissue into the device.

As the devices described herein are RF devices, they deliver radiofrequency energy to a target tissue of interest. The heat generated by the RF energy ablates the tissue, resulting in the formation of scar tissue at the ablation site. As described above, the radiofrequency ablative surgical device is a multielectrode (e.g., "multipolar") radiofrequency ablative surgical device, e.g., a device which transmits RF energy from two or more electrodes (e.g., 2, 3, 4, 5, 6, 7, 8, or more electrodes). When the subject methods employ a multielectrode radiofrequency ablative surgical device, the device may be a bipolar or quadripolar ablative surgical device. The terms "bipolar" and "quadripolar" indicate that the ablation path extends locally between two or four electrodes (respectively) in the device, rather than between one electrode and a general remote, or external electrode. Such devices may be configured to deliver ablation energy to achieve a uniform, superficial depth of ablation between ~500 μm and ~1,000 μm.

Cardiac applications in which the subject devices and methods find use further include those applications described in U.S. Pat. No. 8,617,145, as well as U.S. Application Ser. No. 61/800,534; the disclosures of which are herein incorporated by reference.

The disclosed devices and methods perform ablation protocols in a time-efficient manner. More specifically, by using the subject devices and methods, the total time that an ablation procedure takes can be reduced. The time of such a procedure can be reduced by eliminating or reducing the time required for applying RF energy multiple times to tissue. A reduced time for a surgical process can help prevent fatigue in attending medical staff and can otherwise reduce risk to the patient. For example, a pulmonary vein isolation procedure as described above may be performed with the subject devices in a period of time ranging from 0.5 to 5 min, such as 0.5 to 2 min, including 0.5 to 1 min, which is substantially shorter than the time required using other RF devices.

Kits

Also provided are kits that at least include the subject devices and which may be used according to the subject methods. The subject kits at least include a RF ablation device, e.g., as described above. The kits may further include one or more components to be employed in a given surgical procedure, e.g., trocars, tissue dissectors, etc., e.g., as described in greater detail below, and the like. The components of the kits may be present in sterile packaging, as desired.

In certain embodiments, the kits which are disclosed herein include instructions, such as instructions for using devices. The instructions for using devices are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging etc.). In other embodiments, the instructions are present as an electronic storage data file present on a suitable computer readable storage medium, e.g., Portable Flash drive, CD-ROM, diskette, etc. The instructions may take any form, including complete instructions for how to use the device or as a website address with which instructions posted on the world wide web may be accessed.

In addition, embodiments of the disclosed kits or their components may be used according to any of the embodiments of the methods described herein or combinations thereof.

Methods and Devices for Thorascopically Producing a Cox Maze III Set of Lesions from the Left Side of a Subject As summarized above, the RF tissue ablation devices find use in a variety of methods. One method in which the RF tissue ablation devices find use in the production of a Cox Maze III set of lesions in a subject using a left-sided approach. As such, aspects of the methods include thoracoscopically producing from the left-side of a subject a Cox maze III set of lesions in a subject. By "thoracoscopically producing" or "thoracoscopically" is meant methods which are performed through one or more thoracoscopic body openings using a thoracoscope or a thoracoscopic instrument for procedures such as visualization, surgery, the conduction of diagnostic tests, etc., in or adjacent to the thoracic cavity. Similarly, a "thoracoscopic procedure" is a procedure in which visualization, surgery, a diagnostic test, etc., is performed by gaining access to the chest through one or more thoracoscopic body openings using a thoracoscope, or a thoracoscopic instrument.

By "thoracoscope" or "thoracoscopic instrument" is meant a thin tube-like instrument used to examine or enter the inside of the thoracic cavity of a subject, e.g., the pleural space of a subject. A thoracoscope is a type of endoscope, which is a general term for a thin tube-like instrument for examining the inside of the body. A thoracoscope can have a light and a lens or camera for viewing the inside of the chest, and can also have one or more tools that can be used with a thoracoscope, such as a sewing device, a cutting device, an ablation device, a grasping device, a retracting device, etc. In some embodiments, a single thoracoscopic instrument can have more than one function (e.g., camera and cutting functions, or light and sewing functions, etc.) In addition, although the methods discussed below disclose the use of a particular number of thoracoscopic instruments, the methods of the invention can include using any suitable number of thoracoscopic instruments, such as one or more, two or more, three or more, four or more, etc. In addition, the methods can include use of the thoracoscopic instruments sequentially, or simultaneously, including simultaneous use of bilateral thoracoscopic instruments.

Access to the thoracic cavity can be achieved by percutaneously creating an opening into the chest cavity through a skin incision in the intercostal space (ICS) between two adjacent ribs of the left-side of the subject, and inserting an instrument such as a trocar, cannula, thoracoscope, thoracoscopic instrument or the like through the opening. One or more openings, or "ports" can be created in one or more locations in the intercostal spaces of the chest, depending on the procedure to be performed and the thoracoscopic instruments to be used. One or more thoracoscopes or thoracoscopic instruments can be advanced through at least one of the openings, or thoracoscopic body openings. The creation of additional openings can allow for the use of accessory instruments. In some embodiments, a pneumothorax is created during the thoracoscopic procedure, i.e., $CO_2$ is introduced into the pleural space which surrounds the lung, to collapse the lung and improve the view of the surgical field.

The methods of the subject invention are minimally-invasive methods, such that the thoracoscopic body openings created in the subject's body are small, for example, 3 centimeters or less in greatest dimension, 2 centimeters or less in greatest dimension, 12 millimeters or less in greatest dimension, or 5 millimeters or less in greatest dimension. In some embodiments, all of the thoracoscopic body openings created in the subject's body measure no more than 12 millimeters in greatest dimension. In some embodiments, therefore, "thoracoscopically producing" includes making a thoracoscopic body opening that measures no more than 12 mm in greatest dimension. In some embodiments, "thoracoscopically producing" includes making all of the thoracoscopic body openings no more than 12 millimeters in greatest dimension. This is in contrast to a "mini-thoracotomy" in which an incision which can measure 5 centimeters or 8 centimeters or more is utilized for gaining access to the thoracic cavity. The thoracoscopic methods can allow access to the epicardial surface of the heart.

For practice of the methods described herein, the thoracoscopic body openings or ports are produced unilaterally, i.e., on a single side of the subject's body, and more specifically the left-side of the subject body. While ports on the right side may also be produced for other purposes as desired, e.g., such as shown in FIG. 1 of U.S. patent application Ser. No. 12/358,033 (the disclosure of which is herein incorporated by reference), in some instances only ports on the left-side of the body are produced, such that no ports on the right side of the body are produced. In some embodiments, the number of thoracoscopic body openings or ports may range from 2 to 6 ports, such as from 3 to 5 ports, or 4 ports on the left-side. The number of ports produced can vary depending on the subject, the procedure to be performed, the lesions to be created, and the thoracoscopic instruments to be used.

In one embodiment, the thoracoscopic body openings that are created on the left side of a subject include an opening in the $2^{nd}$ ICS 1 to 2 cm medial to anterior axillary line; an opening in the $3^{rd}$ or $4^{th}$ ICS 1 to 2 centimeters posterior to the anterior axillary line; an opening in the $5^{th}$ ICS in the mid-axillary line; and an opening in the $6^{th}$ ICS in the anterior axillary line. Although the above combination of ICS openings can be used in some embodiments of the invention, the methods can include placement of thoracoscopic body openings which can vary in location, for example, an opening in the $6^{th}$ ICS can be 1 centimeter posterior to the anterior axillary line, or more than one opening can be made in the same ICS.

Figure 5:
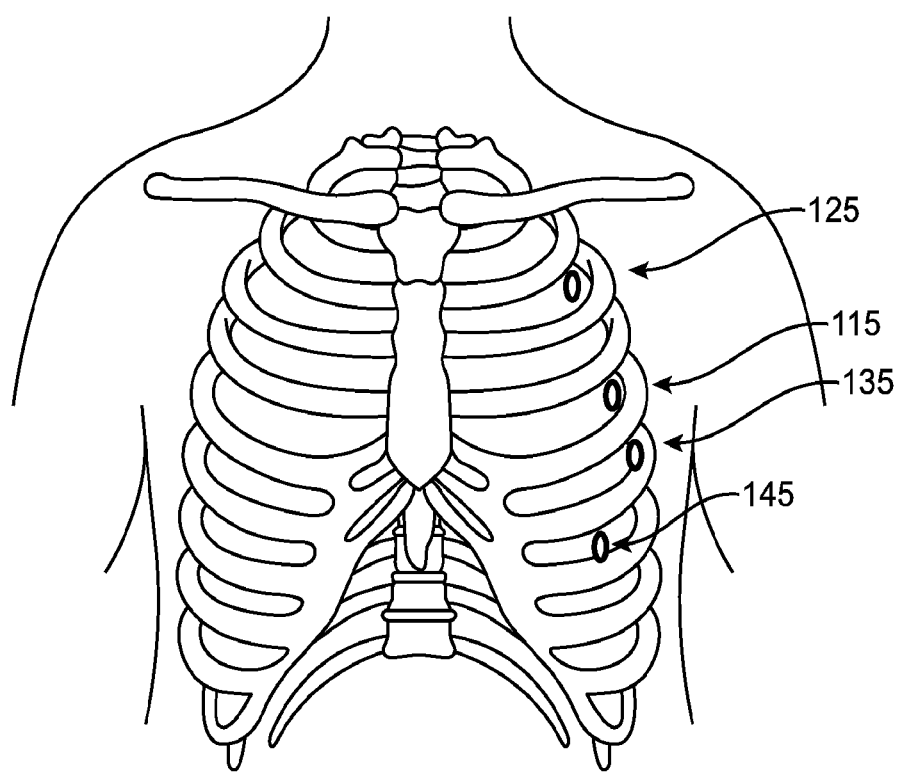
FIG. 5 provides a schematic view of the chest, demonstrating an embodiment of the access ports used to perform the methods of the invention.

A specific example of ports that may be produced in certain embodiments of the invention is shown in FIG. 5. In the embodiment illustrated in FIG. 5, four ports are utilized for performing the methods of the subject invention. The first port, shown as element 115 in FIG. 5, can be placed in the $3^{rd}$ or $4^{th}$ intercostal space (ICS) 1 centimeter posterior to the anterior axillary line. A second port can be placed in the $2^{nd}$ ICS 1 to 2 cm medial to anterior axillary line, shown as element 125 in FIG. 5. A third port can be placed in the $5^{th}$ ICS mid axillary line, shown as element 135 in FIG. 5. The fourth port, element 145 in FIG. 5, can be placed in the $6^{th}$ ICS in the anterior axillary line.

Figure 6:
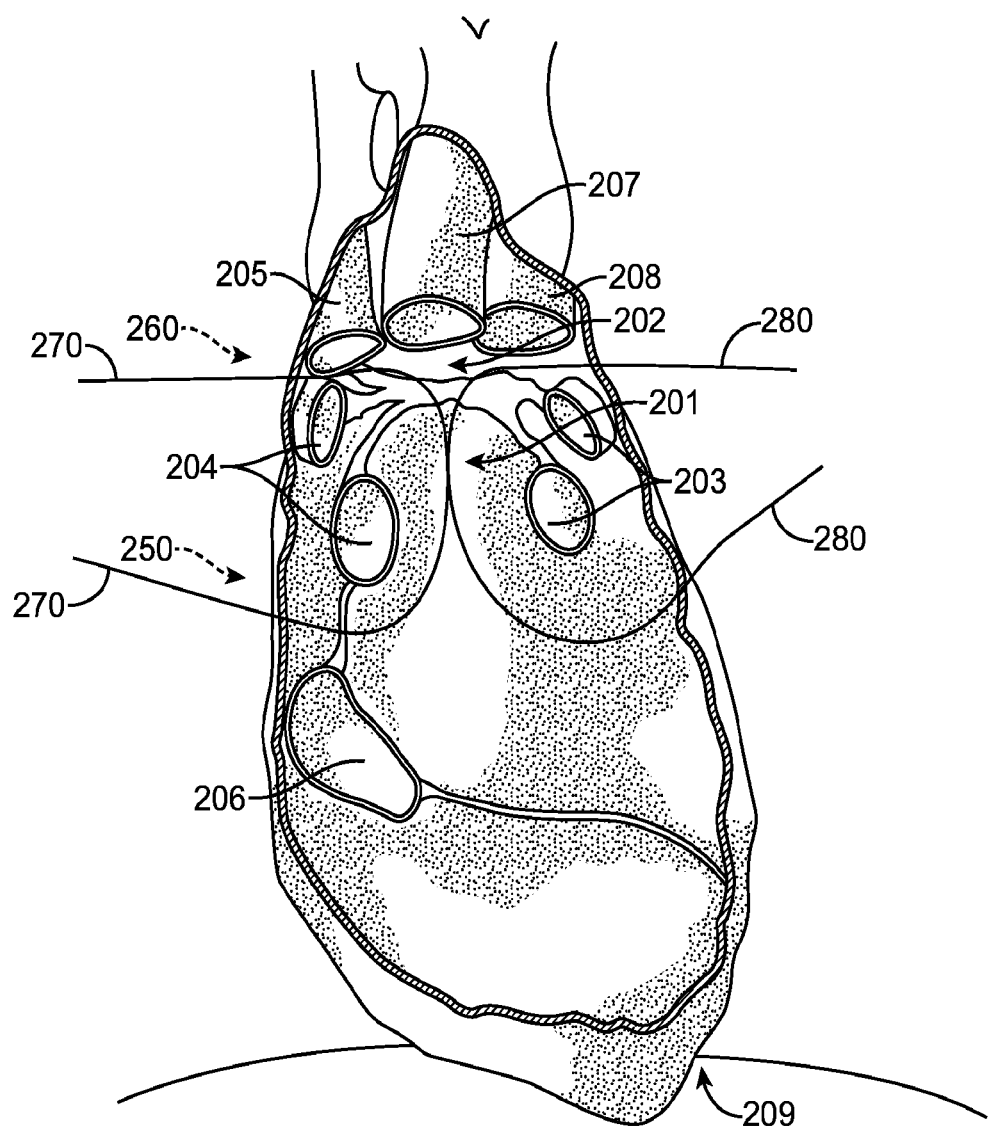
FIG. 6 provides a schematic view of the heart.

FIG. 6 is a schematic view of the posterior wall of heart as viewed from the front, with the remainder of the heart removed for clarity. In FIG. 6, the oblique sinus (element 201) and transverse sinus (element 202) are shown. The oblique sinus is one of two pericardial sinuses (oblique and transverse) which are pouches or cul-de-sacs of the pericardium located behind the heart. The oblique sinus is located behind the left atrium, between the right and left pulmonary veins. Additional anatomic landmarks shown in FIG. 6 include the superior 205 and inferior 206 venae cavae, ascending aorta 207, pulmonary artery 208, and diaphragm 209.

Aspects of the invention include thoracoscopically producing a Cox maze III set of lesions, i.e., without the need for a median sternotomy, or even a mini-thoracotomy (e.g., a chest incision of 5 centimeters). In methods of the invention, a "lesion" or "scar" can be created by ablating cardiac tissue from the epicardial surface of the heart, which is in contrast to methods of creating the lesions from the endocardial surface, or inside surface, of the heart as with an open surgery or a catheter procedure. By "lesion" or "ablation line" is meant an area of cardiac tissue that has been ablated. By "ablation" is meant a process of removing or altering the electrically-conducting tissue in an area of interest, such that the tissue no longer conducts or generates an electrical impulse sufficient to generate or propagate an arrhythmia. The process of ablation can prevent an arrhythmia from developing because the cardiac tissue which provides a trigger for an arrhythmia has been destroyed. The process of ablation can also prevent an arrhythmia from propagating to other areas of the heart by the creation of a line, or lesion, which electrically isolates the tissue and blocks passage of the electrical impulse. Ablation can be performed with a variety of types of energy, such as radiofrequency energy, laser energy, microwave energy, cryothermy, and the like. Ablation "lines" or "lesions" can be focal areas which are separate from other areas of ablation, or they can be contiguous, such they form lines or lesions connected to each other, which can form, for example, a continuous line, or ring, or circle, in order to electrically isolate an area of cardiac tissue.

Accordingly, by "ablation" is meant a process of removing or altering the electrically-conducting tissue in an area of interest (e.g., a GP) such that the tissue no longer conducts or generates an electrical impulse sufficient to generate or propagate an arrhythmia. In some embodiments, ablation can be performed by directly contacting a portion of cardiac tissue with an ablation device, in a manner sufficient to create a lesion. In other embodiments, ablation can be performed by delivery of an ablating agent to cardiac tissue. For example, in some embodiments, an ablation device can be located sufficiently close to an area of cardiac tissue of interest, such that an ablating agent, (e.g., laser energy) is delivered to the cardiac tissue in a manner sufficient to create a lesion. The form of energy used for ablating cardiac tissue can be radiofrequency or cryoablation energy, for example. In some embodiments the ablation is transmural, i.e., extends through the entire heart wall. In other embodiments, the ablation does not extend through the entire thickness of the cardiac wall; however, the degree of ablation may be sufficient to block electrical conduction. Any suitable device can be used for ablation, such as the Isolator Multifunctional Pen disclosed above, or other similar device such as the Cardioblate™ Ablation System (Medtronic, Minneapolis, Minn.), the AFx FLEX 10™ microwave ablation probe (Guidant corporation), the Surgifrost™ Cryoablation System (Cryocath Technologies), or the Epicor™ High Intensity Focused Ultrasound Cardiac Ablation system (St Jude Medical, St Paul, Minn.), for example. Of interest in some embodiments is use of the inter- and intra-RF ablation devices as described above.

The methods of ablation can include contacting a portion of cardiac tissue with an ablation device to form a lesion. The methods can further include repeating the contacting and ablating steps a number of times to produce a plurality of lesions. For example, the contacting step may be performed two or more times, such as three or more, or four or more times, etc. In some embodiments, the contacting and ablating step is performed in the same location. In some embodiments, the contacting and ablating step can be performed in overlapping locations, such that part of a second location overlaps with part of a first ablating location, such as in the case of creating a continuous linear ablation line. In other embodiments, a second ablation step may be in a different location from the first ablation step, as in the ablation of a ganglionic plexus or a complex fractionated atrial electrogram, discussed further below. Although the methods of ablation as described use contact of cardiac tissue in order to achieve ablation, in some embodiments ablation can be achieved by using an ablation device in proximity to cardiac tissue, for example, in delivering an ablation agent to the cardiac tissue.

The devices that can be used with embodiments of the invention are devices that are configured to ablate, or remove, or sufficiently alter electrically-conducting cardiac tissue. In some embodiments, the ablation is achieved by using a form of energy, such as radiofrequency or cryoablation energy. The subject devices are devices that can be used in endovascular, minimally invasive surgical, open surgical, or other interventional procedures. Any suitable device can be used for ablation, such as the ablation devices disclosed above, or other similar devices such as those devices in the Cardioblate™ Ablation System (Medtronic, Minneapolis, Minn.), the AFx FLEX 10™ microwave ablation probe (Guidant corporation), the SurgiFrost®/FrostByte™ Cryoablation System (Cryocath Technologies), or the Epicor™ High Intensity Focused Ultrasound Cardiac Ablation system (St Jude Medical, St Paul, Minn.), for example. However, in some instances the inter- and intra-RF ablation devices as described above, are employed.

An ablation device of the subject methods can be in the shape of a clamp, with an upper and a lower jaw, such that the ablation device is a clamping device. In other embodiments, the ablation device can have an elongated cylindrical shape, such as that of a pen. In some embodiments, the ablation device can have a linear shape, a rectangular shape, a semi-circular shape, an "L" shape, a "U" shape, or any other suitable shape. The configuration of the surface of the ablation device that contacts the tissue can also be any suitable two-dimensional shape such as a line, a square, an oval, a triangle, etc. In some embodiments, the ablation device can further employ suction to pull tissue into the device.

In some instances, e.g., as described in greater detail below, the thoracoscopic ablation device comprises a multipolar electrode element. By multipolar electrode element is meant an element that has more than 2 or more electrodes, e.g., 4 or more electrodes, including 6 or more electrodes. An example of such an electrode is a quadripolar electrode. Such electrodes may be configured to deliver ablation energy to achieve a uniform, superficial depth of ablation between ~500 µm and ~1,000 µm. In some instances the inter- and intra-RF ablation devices as described above, are employed.

The area of cardiac tissue that is ablated will depend on the type of ablation device (e.g., clamp, or pen) and the shape of the portion of the ablation device that contacts the tissue (e.g., rectangular area; circular area). The total area of cardiac tissue that is ablated will further depend on the type and strength of the energy used (e.g., radiofrequency (RF) energy, high intensity focused ultrasound energy) and the length of time that the device is in contact with tissue, for example.

For example, an elongated cylindrical device may have a circular area at one end of the device that of contacts cardiac tissue, and after application of the ablating energy may form an area of ablated tissue that approximates a cone-shaped area of tissue, extending to a particular depth, such as 6 mm, for example. In the case of an ablation device in the shape of a clamp, the area of the ablated tissue between the jaws of the clamp can be a rectangular area, with the approximate dimensions of the clamp. For example, if the jaws of the clamp are each 4 cm long and 5 mm wide, the ablated area can be a rectangular area 4 cm in length and 5 mm in width, with a depth equal to the area of tissue between the jaws of the clamp. In some embodiments, the area of ablated tissue may be greater than the area which was in direct contact with the ablation device, such as 10% greater or more, or 20% greater or more, etc. Furthermore, the shape of the ablated area once ablation has been completed can be any suitable three-dimensional shape such as a cylinder, cone, pyramid, cube, sphere, etc.

The ablation device can include, but is not limited to devices that use radiofrequency (RF) energy, including bipolar radiofrequency energy or bipolar irrigated RF energy, cryoablation, laser energy, microwave energy, thermal energy, a thermo-electric chip device, ultrasound energy, including high intensity focused ultrasound energy, an ablating drug delivery device, and any combinations thereof. For example, the ablation device can be a bipolar radiofrequency (RF) device such as the Isolator® Synergy™ Cardiac Ablation Clamp (Atricure, Inc., Cincinnati, Ohio). This system consists of a power generator, bipolar clamp, and a pacing, sensing, stimulator, bipolar RF pen. The device delivers RF energy with resultant heating of the tissue and can complete a transmural lesion. The term bipolar indicates that the ablation path extends locally between two electrodes in the device, rather than between one electrode and a general remote, or external electrode. Although the current methods can be used with this system, the technique is equally applicable to other types of ablation devices. For example, in some embodiments, the ablation device can be a laser energy device, a microwave energy device, a thermal energy device, an ultrasound device, a cryoablation device, etc. In some embodiments, the methods can include other methods of ablation, such as surgical incision. In some instances the inter- and intra-RF ablation devices as described above, are employed.

The process of ablation can be performed by direct contact of the ablation device with cardiac tissue, and in some embodiments ablation can be performed with delivery of an ablation agent in sufficient proximity to the cardiac tissue of interest. The process of ablation is continued until sufficient conduction block is achieved in the desired area. This can require 1 to 4 or more applications of the device or agent, such as two applications or more, or three applications or more, etc. In addition, the process of ablation can be monitored as the ablation is performed. In some embodiments, the process of ablation can be guided by a feedback parameter, such as impedance, temperature, conductivity, etc. For example, if radiofrequency energy is used, the impedance of the tissue can be monitored and the power output of the device can be designed so that it is inversely proportional to the impedance of the tissue, such that overheating of the tissue does not occur. In some embodiments, the process of ablation can be continued for a specific period of time, which can be determined by the thickness or composition of the tissue to be ablated, or the anatomical location of the tissue to be ablated, for example.

The subject methods may also include intraoperative electrophysiologic testing of the cardiac tissue to confirm the presence of a lesion. This step can be used to determine whether or not a first ablating step produced sufficient removal or alteration of the electrical conduction of the tissue in order to block electrical conduction. If it is determined that sufficient ablation has not been achieved, the contacting and ablating steps can be repeated until sufficient conduction block is confirmed. Intraoperative testing for conduction block can include sensing for electrical signals on either side of an ablation line, for example, to verify that the ablation line is complete (e.g., transmural) and continuous, and that electrical impulses are not crossing the ablation line. Testing for conduction block can also include sensing for electrical signals on the ablation line that has been created. In some embodiments, a sensing pen, such as a bipolar radiofrequency pen, can be placed on the ablation line itself, and the strength of the sensed electrical signals can be determined. For example, it may be determined that a sensor placed on an ablation line may demonstrate a reduction in amplitude of the EKG, such as an 80%, or 90% reduction in amplitude of the EKG, which can be an indication of the degree of ablation. Intraoperative electrophysiologic testing can be performed, for example, by measuring the change in conductive properties of the tissue as it is being ablated. In some embodiments, intraoperative testing can include testing for uni- or bi-directional block. The presence of uni- or bi-directional block can be confirmed with a sensing device, such as the combination ablation and sensing device disclosed above. For example, cardiac tissue can be tested for "entrance" block, meaning that an electrical signal or impulse cannot pass from the atrial side of a lesion to the pulmonary veins. If a subject is in sinus rhythm, the tissue can also be tested for "exit" block, meaning that an electrical signal or impulse cannot pass from the pulmonary veins to the atrial tissue on the other side of an ablation line. If both "entrance" and "exit" block is present, then bidirectional block can be confirmed. If the subject is not in sinus rhythm (e.g., atrial fibrillation), only unidirectional "entrance" block can be confirmed, as it is not possible to evaluate whether or not an electrical signal has traveled from the pulmonary veins to the atrial tissue in the presence of atrial fibrillation.

Figure 7:
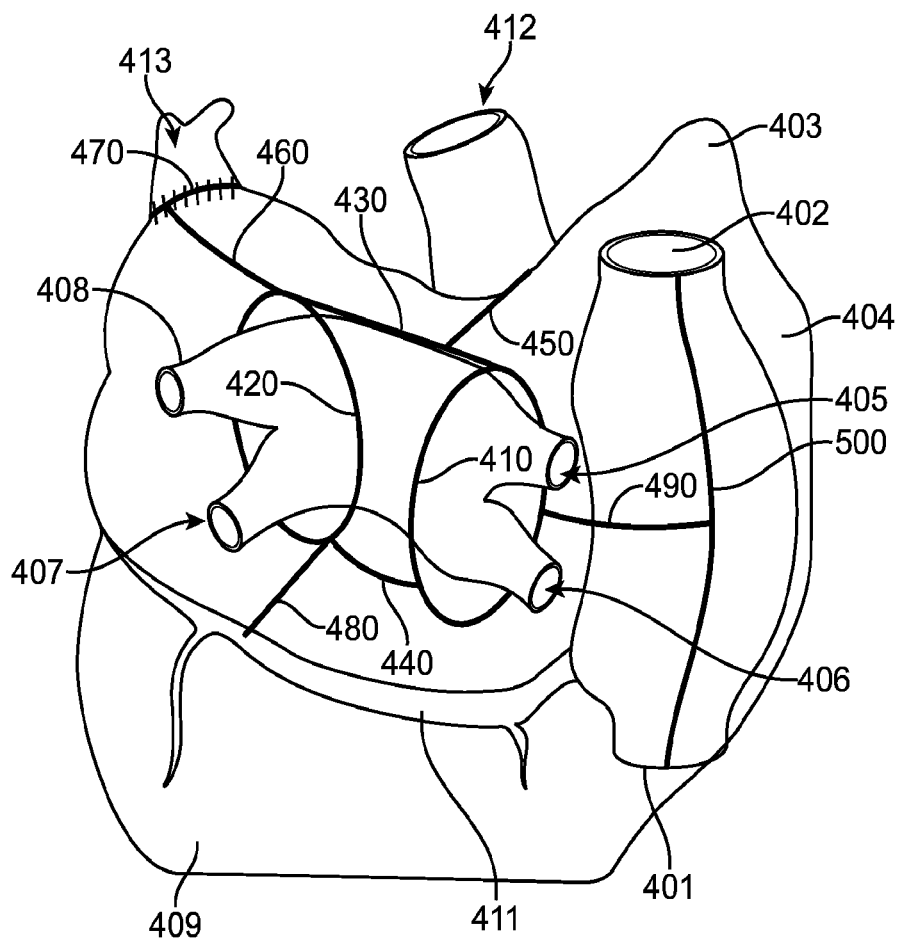
FIG. 7 provides a schematic view of the heart, demonstrating a map of the ablation lesions that can be created using the methods of the subject invention.

By "Cox maze III" set of lesions is meant a group of lesions chosen from among the following ablation lines: a right pulmonary vein encircling ablation line 410 as shown in FIG. 7, a left pulmonary vein encircling ablation line 420, a superior connecting ablation line connecting the right and left pulmonary vein encircling lines 430, an inferior connecting ablation line connecting the right and left pulmonary vein encircling lines 440, an ablation line connecting the superior ablation line to the fibrous trigone 450, an ablation line connecting the superior ablation line to the base of the left atrial appendage 460, and an ablation line extending from the inferior connecting ablation line to the coronary sinus 480. The combination of ablation lines 410, 420, 430, and 440 comprises what is known as the "box lesion" set. As such, in some instances, the Cox maze III lesion set produced by methods of the invention is a box lesion set.

In some embodiments, the set of lesions making up the Cox Maze III lesion set according to the methods of the subject invention further includes one or more additional lesions in addition to the box lesion set. In some instances, Cox Maze III lesion sets of the invention may include amputation of the left atrial appendage, or a left atrial appendectomy (element 470). In some embodiments, the set of lesions produced by methods of the invention further includes an ablation line in the posterolateral wall of the right atrium connecting the superior vena cava to the inferior vena cava, shown as element 500 in FIG. 7. In some embodiments, the set of lesions also includes an ablation line connecting the right pulmonary vein encircling ablation line to an ablation line in the posterolateral wall of the right atrium connecting the superior vena cava to the inferior vena cava, shown as element 490 in FIG. 7. In some embodiments, the methods of the subject invention further include ablation of autonomic ganglionic plexi on the epicardial surface of the atrium. In some embodiments, the methods of the subject invention can include ablation of complex fractionated atrial electrograms, discussed further below.

In some instances, the methods include first identifying a subject in need of surgical treatment for a cardiac arrhythmia. A subject who needs surgical treatment for an arrhythmia can include, for example, subjects who are symptomatic, subjects who are asymptomatic but cannot be adequately anticoagulated to reduce their risk of stroke, subjects who have failed medical therapy, subjects who have failed catheter ablation, subjects who cannot tolerate the side effects of anti-arrhythmic drugs, or subjects who choose surgical ablation as a preferred method.

A patient in need of surgical treatment for a cardiac arrhythmia can be prepared for surgery in the conventional manner. General anesthesia, when desired, can be provided using any convenient protocol, e.g., via administration of an anesthetic agent with a double-lumen endotracheal tube in order to provide single lung ventilation. In some embodiments, transesophageal echocardiography monitoring is performed during the entire procedure.

The methods of the subject invention can be performed on a beating heart, i.e., without cardiopulmonary bypass, and the methods can also be performed in a patient on cardiopulmonary bypass, i.e., a stopped heart. The procedure may be performed on the right side first, followed by the left side as outlined below, or alternatively, the procedure may be performed on the left side first, followed by the right side.

For a left thoracoscopic approach, the operating table can be tilted slightly to the right side with a slight tilt, such as a 15 degree tilt. After the left lung is deflated, one or more openings can be created in the left side of the chest. In one embodiment, four ports can be utilized for performing the methods of the subject invention, as shown in FIG. 5. The first port, shown as element 115 in FIG. 5, can be placed in the $3^{rd}$ or $4^{th}$ intercostal space (ICS) 1 centimeter posterior to the anterior axillary line. A thoracoscope can be introduced and the left hemithorax visually inspected. Humidified $CO_2$ can be introduced into the thoracic cavity at a pressure sufficient to allow adequate visualization for the methods of the invention (e.g., 8 mm Hg pressure). A second port can be placed in the $2^{nd}$ ICS 1 to 2 cm medial to anterior axillary line, shown as element 125 in FIG. 5. The placement of this most cephalad port on the left allows for the exposure for completion of the superior connecting ablation line in the roof of the left atrium. The most cephalad port (e.g, a port in the $2^{nd}$ ICS) can also utilized in the creation or completion of the ablation line from the superior pulmonary vein connecting ablation line across the dome of the left atrium to the fibrous trigone (element 450). A third port can be placed in the $5^{th}$ ICS mid axillary line, shown as element 135 in FIG. 5. The fourth port, element 145 in FIG. 5, can be placed in the $6^{th}$ ICS in the anterior axillary line. A thoracoscopic grasping forceps can be introduced through the most caudal port. A second opening can be created in the pericardium on the left side to allow access to the epicardial surface of the heart. In some embodiments, the pericardium can be opened in the most dependent portion posterior to the left phrenic nerve and the opening can be then extended to the level of the diaphragm. The pericardial opening can be enlarged posterior and parallel to the phrenic nerve extending cephalad and superior to the right pulmonary artery. An endograsper or endoKittner can then be introduced through the third port. One or more traction sutures can be placed on the edges of the pericardium, to expose the left atrial appendage in its entirety. In some embodiments, this is facilitated utilizing an Endo Stitch™ (Autosuture™, Covidien, Mansfield, Mass.), or other similar suture device.

A combination ablation and sensing device as described above can be introduced into the thoracic cavity via the third port. The sensing portion of the device can be used for sensing pulmonary vein potentials, to create a baseline map of the left pulmonary vein potentials. Additionally, in some embodiments, autonomic ganglionic plexi can be mapped with high-frequency stimulation and then focally ablated, as disclosed above for the right side.

In some embodiments, the ligament of Marshall and posterior pericardial attachments can be divided, or separated, from the pulmonary artery down to the dome of the left atrium, and then ablated. The ligament of Marshall is a vestigial structure of the vein of Marshall which can also be a source of arrhythmia. Exposure to allow ablation of the ligament of Marshall can be facilitated by using an instrument inserted through the superior port, e.g., the port in the $2^{nd}$ or $3^{rd}$ ICS, which is suitable for retracting tissue (e.g., an endoscopic fan retractor, or a soft tissue dissector such as an endoscopic Kittner) which can retract the left atrial appendage medially and caudally. Simultaneous retraction of the left pulmonary artery cephalad, or in a superior direction, can allow access to the ligament of Marshall.

After the ligament of Marshall is divided and ablated, a dissector, such as the Wolf dissector, can then be introduced through the $5^{th}$ ICS port incision (element 135 in FIG. 5) with a guiding element, such as the Glidepath™ Transfer Tape or a red rubber catheter attached. The soft tissue dissector can be placed into the oblique sinus, and maneuvered until the tip passes through the transverse sinus superior and medial to the left superior pulmonary vein. Alternatively, the guiding catheter can be placed from the transverse sinus to the oblique sinus. The Glidepath catheter is grasped and pulled out of the chest, and the dissector disarticulated and removed. The guiding catheter or tape now forms a path between the transverse sinus and the oblique sinus. The distal end of the Glidepath catheter, which has been attached to an ablation device, can then be introduced into the left hemithorax. The guiding element, such as a catheter, can be used to guide one jaw of a clamp behind the left pulmonary veins while the other jaw is passed in front of the veins, e.g., as desired. The process of ablating the atrial tissue surrounding the pulmonary veins ablation can be continued until sufficient conduction block is achieved, such as with 1 to 4 applications of the clamp, including two applications or more, or three applications or more, etc.

Figure 8:
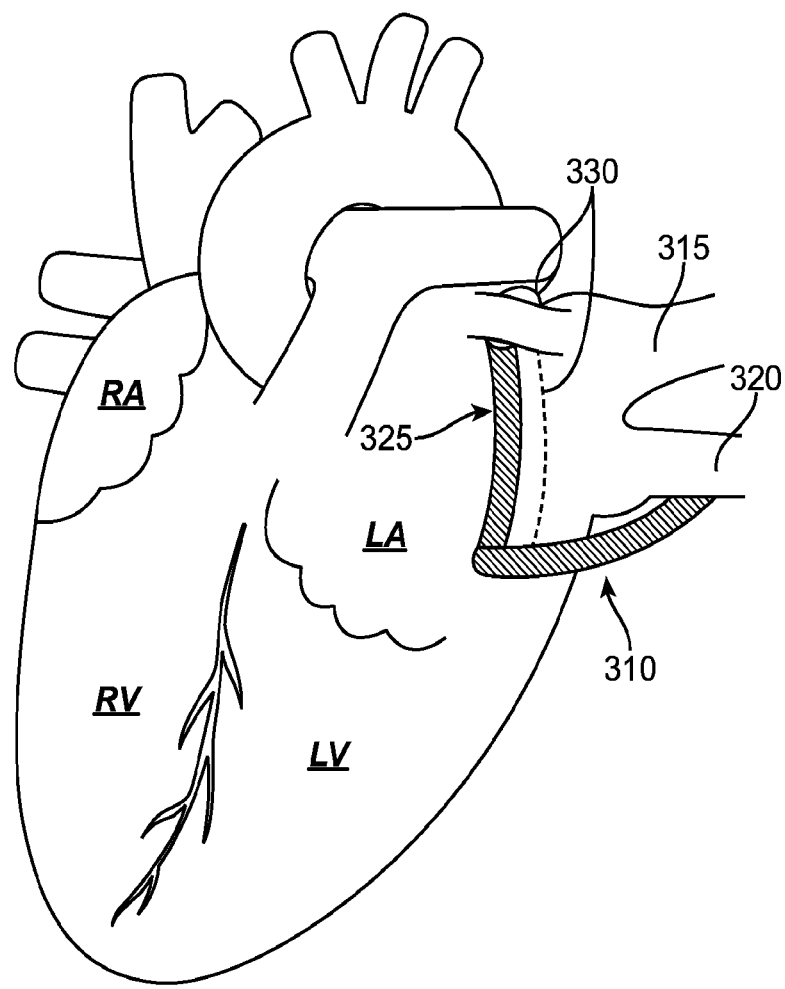
FIG. 8 provides a schematic view of the heart, demonstrating an embodiment of the clamping method which can be used according to methods of the invention.

Clamping of the left pulmonary veins is shown for illustration in FIG. 8. In this view, the left atrium is indicated as LA, the right atrium is indicated by RA, the left ventricle by LV, and the right ventricle by RV. Clamping of the right pulmonary veins, although not shown, can be performed in a similar manner. In some embodiments, while clamping the right pulmonary veins, some or all of the inter-atrial groove tissue, where ganglionic plexi can be located, can be included in tissue to be ablated. The ablation clamp 310 is shown, in this embodiment, as having one jaw in front (element 325) of the left superior pulmonary vein 315 and the left inferior pulmonary vein 320, and one jaw behind the veins (element 330). The process of ablating the atrial tissue surrounding the pulmonary veins ablation can be continued until sufficient conduction block is achieved, such as with 1 to 4 applications of the clamp, such as two applications or more, or three applications or more, etc. Bidirectional block (e.g., an electrical signal is not transmitted from either direction) can then be confirmed with a sensing device, such as the combination ablation and sensing device disclosed above. In some embodiments, each pulmonary vein can be tested individually for bidirectional block for both pacing and sensing. After bidirectional block is confirmed, the ablation device, such as a clamp, and the guiding catheter or tape can be removed. This completes the ablation, or electrical isolation of tissue around the right set of pulmonary veins, which is shown as element 410 in FIG. 7.

Figure 9A:
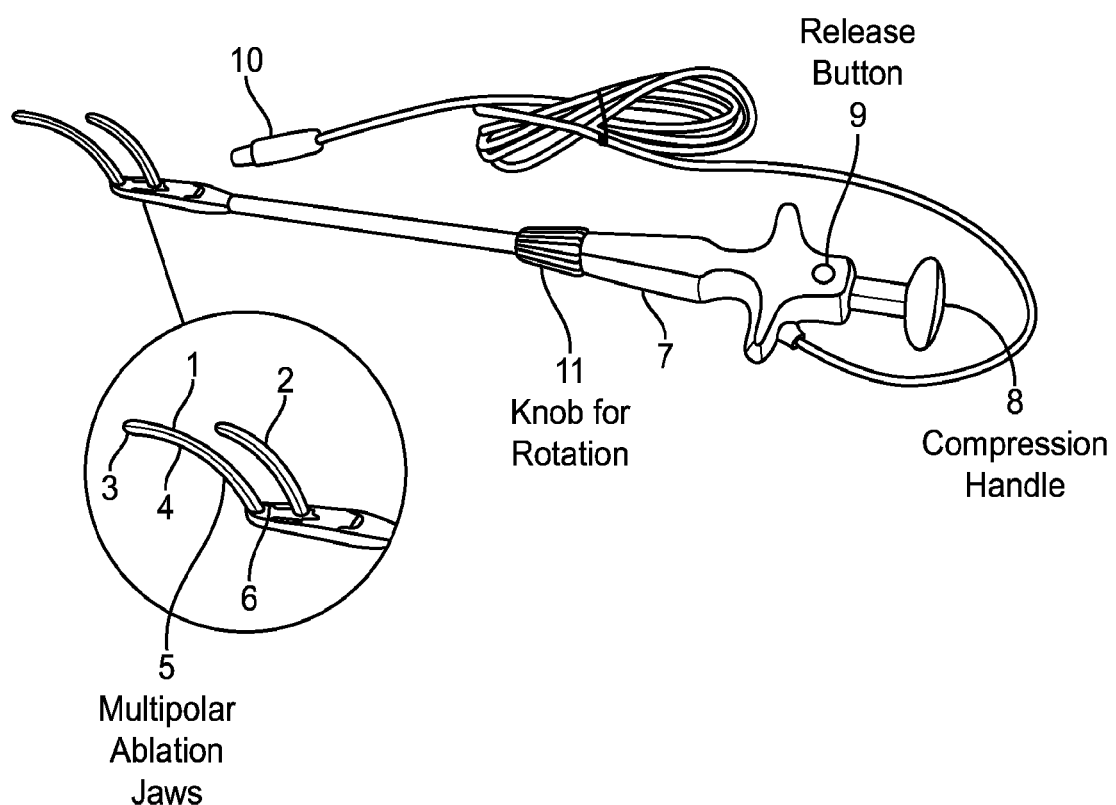
FIGS. 9A and 9B provide views of various multipolar ablation devices according to certain embodiments of the invention.

In some instances, a multipolar clamping ablation device as shown in FIG. 9A may be employed, which device may be an inter- and intra-RF ablation device, e.g., as described above. The clamping ablation device as depicted in FIG. 9A includes a distal end claim element, which element includes first and second multipolar ablation jaws which are configured or dimensioned to contact an anatomical structure, e.g., cardiac structure, such as a partial encircling of pulmonary veins, during the procedure as described above. Each ablation jaw or prong may vary in dimensions, ranging in some instances from 0.5 to 10 cm, such as 1 to 5 cm, e.g., 1 to 3 cm. The distances between the jaws may vary and be variable, e.g., being operably connected to an operator, such as a compression handle as shown, at the proximal end of the device. The distance may, in some instances range from 0.1 to 2 cm, such as 0.1 to 1 cm, e.g., 0.1 to 1 cm, such as 0.1 to 0.5 cm. Each of the multipolar ablation jaws may include two or more electrodes, e.g., three or more electrodes, four or more electrodes, five or more electrodes, six or more electrodes, etc., where in some instances the number of electrodes on each jaw is more than two, and in some instances is an even number. In addition, the number of electrodes on each jaw may differ from each other. The device further includes an operating handle at the proximal end, which is separated from the distal end by a shaft. The shaft may have a variable length, with the length being chosen to provide for access to the target anatomical site and also ease of use. In some instances the length of the shaft may range from 5 to 100 cm, such as 10 to 75 cm, e.g., 25 to 50 cm. Associated with the proximal handle may be steering element, such as a rotation knob. The handle may be operatively connected to an ablative energy source, e.g., an RF source, such as via a cable. It should be noted that while this device is described in terms of this particular application, it is not limited to use in the methods described herein, but may be employed in yet other methods.

Figure 9B:
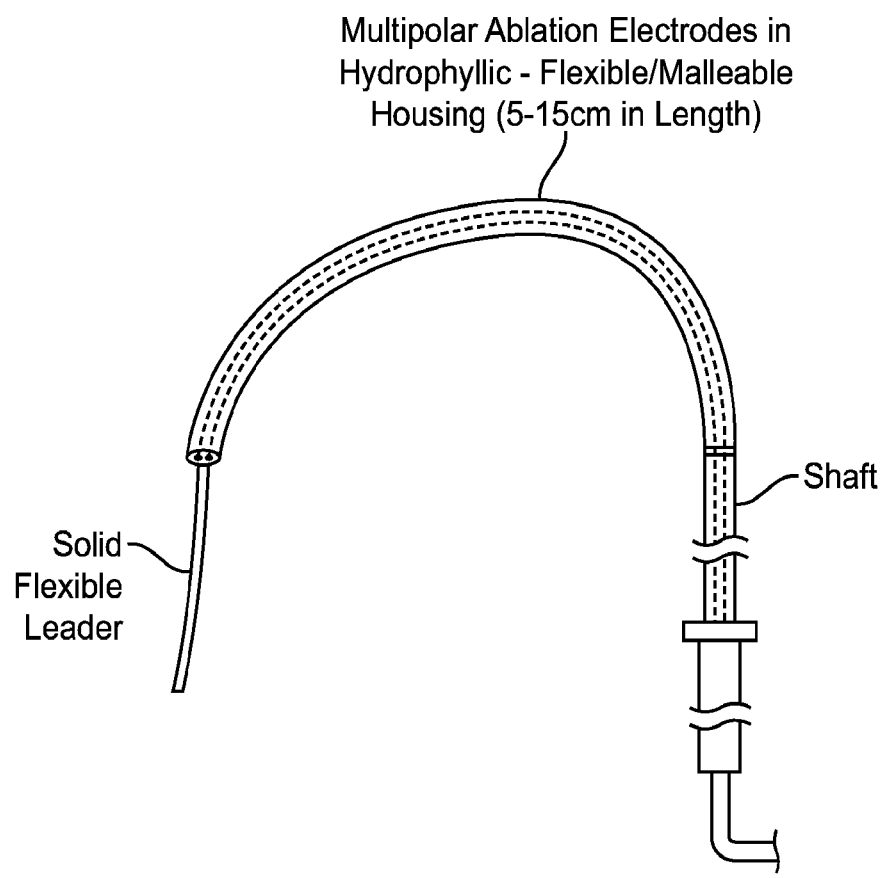

Another device that may be employed to produce curvilinear ablation lines, such as lines 410 and 420, is depicted in FIG. 9B. The device depicted in FIG. 9B includes a distal end flexible multipolar electrode element, e.g., as described above, which is configured to contact a target anatomical site, e.g., as described above. The device may be inter- and intra-RF ablation device, e.g., as described herein. The length of the flexible element may vary, ranging in some instances from 2 to 20 cm, such as 5 to 15 cm. The multipolar electrode element may include multiple electrodes, e.g., as described above, present in flexible housing, e.g., made of a physiologically acceptable material, which may be coated with a hydrophilic coating, e.g., as described elsewhere herein. Located at the distal end of the device may be a solid flexible leader element, which may be configured to be pulled by another device for use in placement of the multipolar flexible element in the desired ablation location. At the proximal end of the flexible multipolar electrode element may be a shaft, e.g., as described above, and a handle, which may also be as described above. It should be noted that while this device is described in terms of this particular application, it is not limited to use in the methods described herein, but may be employed in yet other methods.

In some embodiments, after ablation has been performed, the cardiac tissue can be tested for sufficient conduction block. In some embodiments, each pulmonary vein is tested individually for bidirectional block for both pacing and sensing. After sufficient conduction block is confirmed, the ablation device and the guiding element can be removed. This completes the ablation, or electrical isolation of tissue around the left set of pulmonary veins, which is shown as element 420 in FIG. 7. Where desired, the ablation device may have integrated sensing ability to perform this testing step. In yet other embodiments, a device such as the Cobra Fusion System from Estech corporation, San Ramon Calif. may be employed.

Figure 10A:
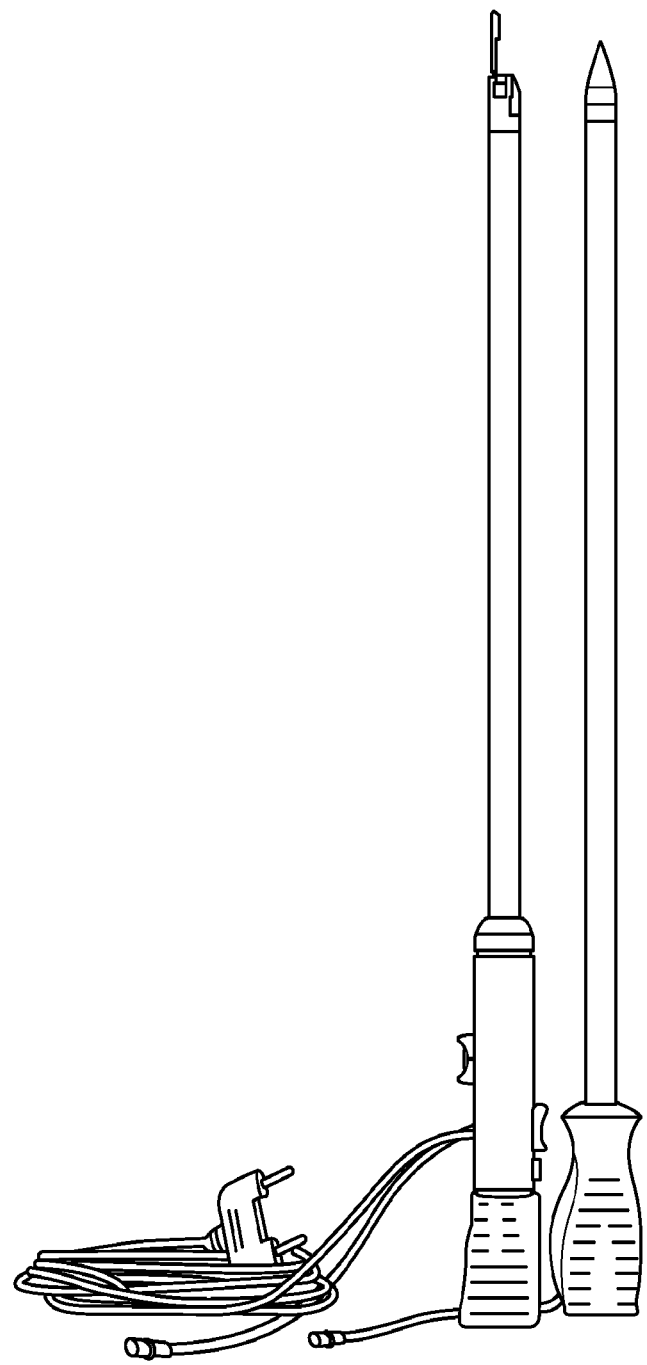
FIGS. 10A and 10B provide depictions of thoracoscopic dissector devices dimensioned for left-sided thoracoscopic applications, in accordance with an aspect of the invention.
Figure 10B:
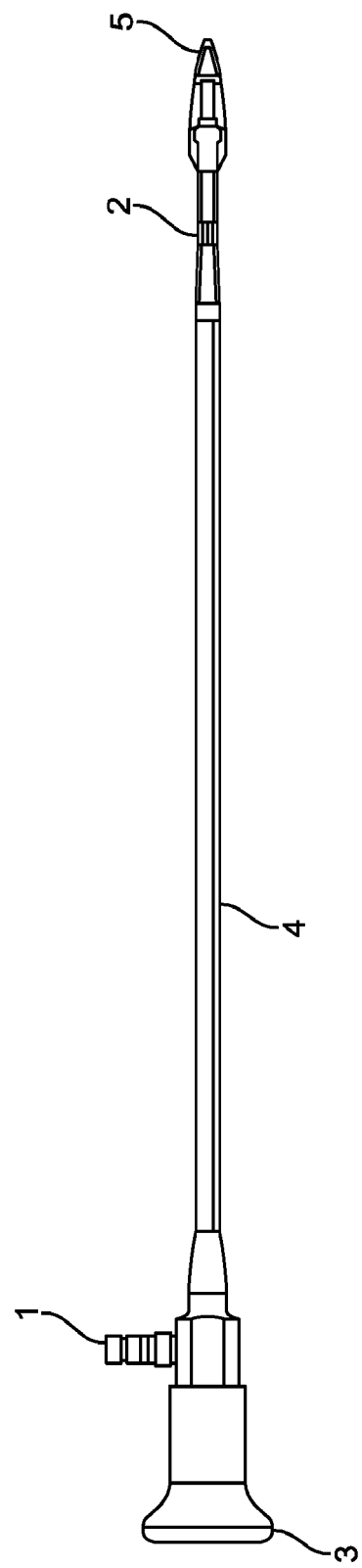

Next, an endoscopic dissector rod with an atraumatic conical tip having centering rings and $CO_2$ delivered at the tip is inserted into the transverse sinus. The confluent tissue between the superior vena cava, left atrium and right pulmonary artery is dissected to allow entry to the right pericardial space lateral to the right atrium. Additionally, the endoscopic dissector rod with atraumatic conical tip can then be used to bluntly dissect the posterior pericardial attachments of the dome of the left atrium, thereby freeing the posterior aspect of the left atrium from the posterior pericardium. The endoscopic dissector rod is then placed caudal to the left inferior pulmonary vein and placed in the oblique sinus and the confluent tissue between the right inferior pulmonary vein and inferior vena cava is divided. This step also allows entry to the pericardial space lateral to the right atrium. In this step, any convenient endoscopic dissector rod may be employed. Examples of such devices include, but are not limited to: the dissector device of the VirtuoSaph® Plus Endoscopic Vessel Harvesting System (Terumo) (dissector device includes an atraumatic conical tip, $CO_2$ delivery component at the tip, PTFE shaft and ergonomic handle with grip (See FIG. 10A), the dissector device of the Vasoview Hemopro 2 Endoscopic Vessel Harvesting System (Maquet) (the dissector device includes a reusable 7 mm extended length endoscope having a stainless steel shaft 4 housing optical and illumination components, where the proximal end has an eyepiece 3 for camera adapter attachment, and a light post for light cable connection, a removable Dissection Tip 5 which attaches to the distal end of the shaft, and consists of a clear, blunt-tipped cone at the distal end for tissue dissection and visualization, and a larger bulb at the proximal end for dilation of the cavity, e.g., as shown in FIG. 10B) and the like. In some instances, a dissector specifically adapted to use in the methods described herein is employed, e.g., one in which the shaft is shorter than that of the devices shown in FIGS. 10A and 10B, e.g., where the length may be 95% or less, 90% or less, 85% or less, 80% or less, 75% or less, 60% or less, 50% or less, than the length of the shaft of the devices shown in FIGS. 10A and 10B. Where desired, at least a portion of the outer surface of the dissector may be coated with a physiologically acceptable hydrophilic coating. Such coatings include, but are not limited to: Lubrlast (AST Products), the coating described in Nagaoka et al., Biomaterials. 1990 August; 11(6):419-24, hyaluron based hydrophilic coatings, etc. It should be noted that while this device is described in terms of this particular application, it is not limited to use in the methods described herein, but may be employed in yet other methods.

The heart can then be retracted anteriorly to perform an inferior epicardial ablation line 440 in FIG. 7 in continuity with the left pulmonary vein encircling ablation line 420. Conveniently, an ablation and sensing device may be employed. The superior epicardial ablation line 430 is performed by connecting to the left pulmonary vein encircling ablation line 420. Additional ablation lines can then be made from the mid-portion of the left atrial appendage down to its base, shown as element 460, which can be connected to the left pulmonary vein encircling ablation line 420.

Figure 11:
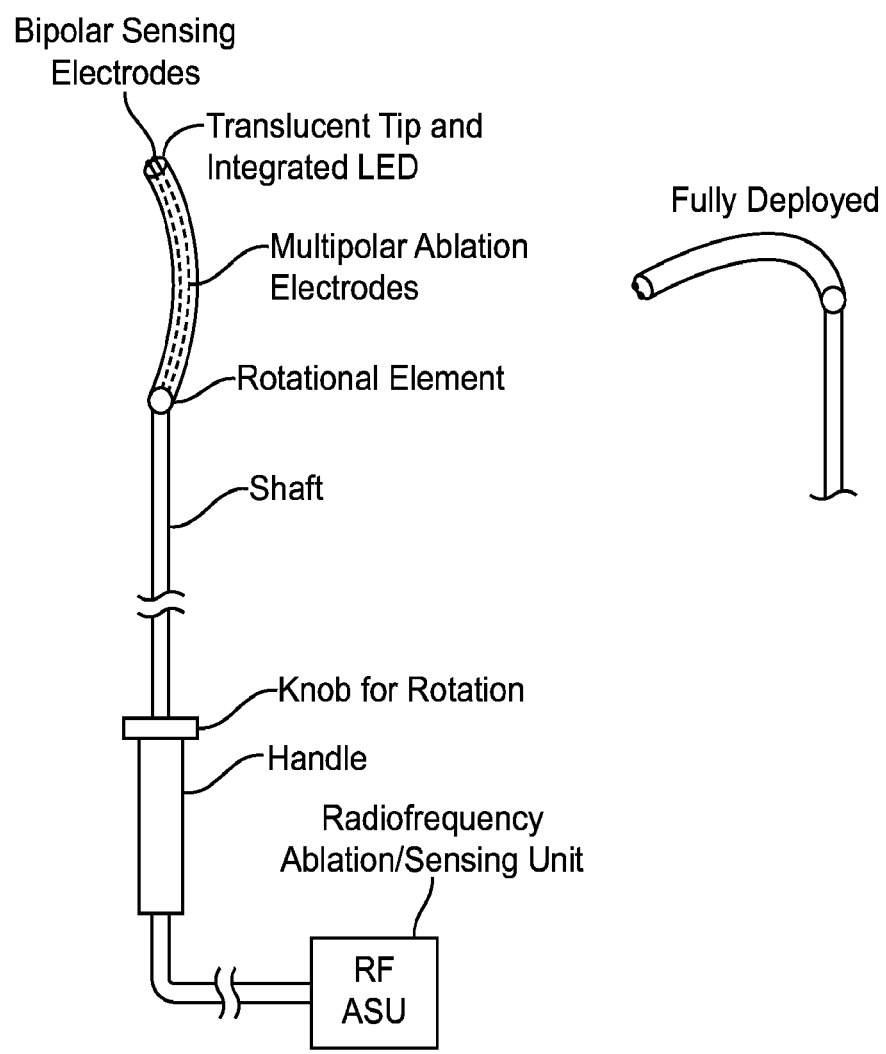
FIG. 11 provides a view of a linear multipolar articulating ablation sensing device according to an embodiment of the invention.

For the above steps, in some instances an articulating linear combination ablation and sensing device may be employed, where the device is a multipolar device, e.g., as described above. Of interest in some embodiments is a device that is a modification of that described in PCT/US2007/004908; the disclosure of which is herein incorporated by reference. An example of an articulating linear combination ablation and sensing device is depicted in FIG. 11. As shown, the device includes a distal end having an articulating multipolar ablation element with bipolar sensing electrodes at the distal tip. Also present at the distal tip are illumination elements, e.g., LEDs. The length of the ablation tip may vary in dimensions, ranging in some instances from 0.5 to 10 cm, such as 1 to 5 cm, e.g., 1 to 3 cm. At the proximal end of the flexible multipolar electrode element may be a shaft, e.g., as described above, and a handle, which may also be as described above. It should be noted that while this device is described in terms of this particular application, it is not limited to use in the methods described herein, but may be employed in yet other methods. The RF ablation device may be inter- and intra-RF ablation device, e.g., as described herein.

Figure 12A:
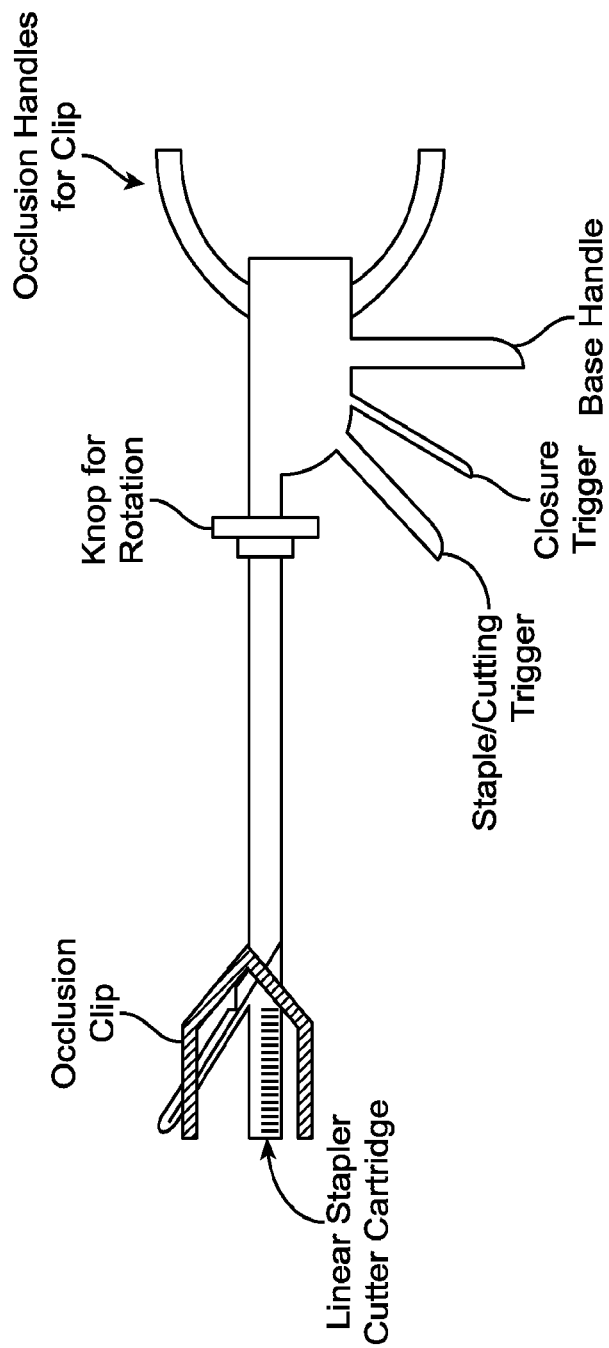

In some embodiments, the methods of the subject invention further include amputation of the left atrial appendage (element 470). The left atrial appendage can be a frequent source of thromboemboli in patients with atrial fibrillation. In some instances, the left atrial appendage can be occluded and amputated with an integrated endoscopic occlusion-amputation device. An example of such a device is illustrated in FIGS. 12A and 12B. As shown in FIG. 12A, the distal end of the device includes the linear stapler cutter cartridge, as depicted in greater detail in FIG. 12B, and an occlusion clip. The device further includes a shaft separating the distal end from the proximal end handle, where the shaft may have dimensions e.g., as described above. The handle includes operators for the distal end elements, including a staple, cutting trigger or actuator, a closure trigger or actuator, a based handle and occlusion handles for the clip. Also present is a rotation knob. It should be noted that while this device is described in terms of this particular application, it is not limited to use in the methods described herein, but may be employed in yet other methods. In FIG. 12B, a cross sectional view of the distal end of a such a device is shown which encompasses a Weck type clip, e.g., varying from 35 to 55 mm in length (which may be covered with a convenient material, e.g., dacron), and an endoscopic linear stapling and cutting device. Alternatively, the clip occlusion aspect of the device can be made of inert implantable substance such as titanium or a bioabsorbable substance like PDS (polydioxanone suture).

Figure 13:
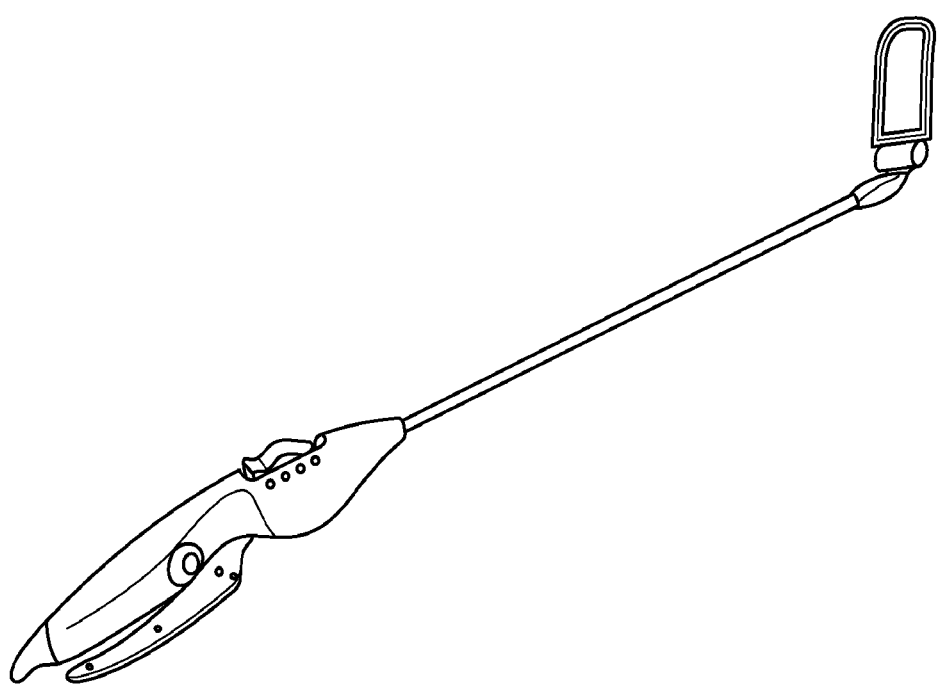
FIG. 13 provides of a device which may be employed in accordance with an aspect of the invention.

Alternatively, an endoscopic no-knife stapling device, such as an Ethicon™ EZ 45 NK device (Ethicon Endo-Surgery, Inc., Cincinnati, Ohio) or a left atrial appendage clip (LAA) clip (AtriCure Inc., Westchester, Ohio; See FIG. 13) which is placed at the base of the appendage, may be employed. The line of exclusion for the left atrium is shown as element 470 in FIG. 7. Placement can be confirmed by tranesophageal echocardiography. After the exclusion is complete, the left atrial appendage can be amputated with a cutting stapling device, such as an Ethicon EZ 45 K device, and the appendage removed.

After removal of the left atrial appendage, visualization of the dome of the left atrium and transverse sinus is enhanced. Utilizing an articulating linear multipolar combination ablation, pacing and sensing device, e.g., as described above, linear ablation lines can be performed to the anterior fibrous trigone as shown as element 450 in FIG. 7. An additional ablation line can be made from the lesion connecting the right and left inferior pulmonary veins 440 to the coronary sinus, shown as element 480 in FIG. 7.

Where desired, additional lesions can be produced from the left thoracoscopic approach because of the articulating arm of the linear quadripolar combination ablation, pacing and sensing device. These linear ablation lines include a vertically-oriented ablation line connecting the superior vena cava (SVC) to the inferior vena cava (IVC), which can be made in the same manner as disclosed above, shown as element 500 in FIG. 7. Furthermore, a T-ablation line can be formed which connects the vertical line connecting the SVC to the IVC (element 500) with the lateral aspect of the encircling right pulmonary vein isolation ablation line (element 410), thereby creating a continuous line across the lateral aspect of the atrial septum. This lesion is shown as element 490 in FIG. 7.

Elements of the Cox maze III set of lesions that can be produced with the methods of the subject invention therefore can include a right pulmonary vein encircling ablation line 410 as shown in FIG. 7, a left pulmonary vein encircling ablation line 420, a superior connecting ablation line connecting the right and left pulmonary vein encircling lines 430, and an inferior connecting ablation line connecting the right and left pulmonary vein encircling lines 440. The combination of ablation lines 410, 420, 430, and 440 comprises what is known as the "box lesion" set. In addition, an ablation line connecting the superior ablation line to the fibrous trigone 450, an ablation line connecting the superior ablation line to the left atrial appendage 460, a left atrial appendectomy 470, and an ablation line extending from the inferior connecting ablation line to the coronary sinus 480 can additionally be produced. In some embodiments, the set of lesions can include an ablation line in the posterior wall of the right atrium connecting the superior vena cava to the inferior vena cava 500, and an ablation line connecting the right pulmonary vein encircling line to an ablation line in the posterior wall of the right atrium connecting the superior vena cava to the inferior vena cava 490. In addition, in some instances the methods can include ablation of autonomic ganglionic plexi. In some embodiments, the methods also include ablation of complex fractionated atrial electrograms, as discussed above.

Although the above ablation lines or lesions have been described in a particular order, the methods of the invention can also include creation of the lesions in any suitable order. For example, the superior epicardial ablation line 430 in FIG. 7 can be completed by connecting to the left pulmonary vein encircling ablation line 420, and then the inferior epicardial ablation line 440 can be completed by connecting this line to the left pulmonary vein encircling ablation line 420.

In some instances, the methods of the subject invention further include focal ablation of one or more complex fractionated atrial electrograms (CFAEs). CFAEs are areas of cardiac atrial tissue with characteristic morphologically distinct electrograms that may contribute to the initiation and/or propagation of arrhythmias. CFAEs can be located by interrogation from the epicardial surface with a sensing device, such as a sensing pen. One or more complex fractionated atrial electrograms can be ablated from the epicardial approach, using the devices as disclosed above. CFAEs can be sensed and ablated in both left and right atria, as well as in both the superior and inferior vena cavae. The methods can include performing the ablating steps one or more times until it is determined that the CFAE has been ablated (e.g. the characteristic morphology of a complex fractionated atrial electrogram is no longer detected in the region that has been ablated). Further details of techniques of mapping and ablation of CFAEs that can be adapted for use with the subject methods are disclosed in the publication by Nademanee, et al., entitled "A new approach for catheter ablation of atrial fibrillation: mapping of the electrophysiologic substrate". Following the completion of the ablation procedure, a chest tube can be inserted for venting and the right lung re-inflated.

Furthermore, although the methods of producing ablation lines disclosed above have been described as being performed sequentially, such that the ablation lines are produced first on one side followed by the other side, in some embodiments the methods of the invention can also include the production of ablation lines from both sides simultaneously. The methods of the subject invention can also include the simultaneous use of thoracoscopic instruments from both sides, such as for example, if a thoracoscopic instrument inserted from the left is used to produce an ablation line, and a thoracoscopic instrument inserted from the right is used for retraction, for illumination, etc.

After completion of the ablation procedure as outlined above, the set of lesions that have been created can be tested by attempting to induce an arrhythmia, e.g., atrial fibrillation, by atrial burst pacing. For example, the cardiac tissue can be stimulated at 20 mA for 5 seconds. If an attempt to induce an arrhythmia results in sustained AF, for example, then this can indicate that atrial tissue with the potential of generating or maintaining AF persists. Sustained atrial fibrillation can be defined as AF lasting ≥10 minutes. If an arrhythmia can be induced at the conclusion of the procedure, then additional ablation can be performed. This can include additional ablation, for example, in positive GP sites, or additional ablation in one of the connecting ablation lines, e.g., the connecting ablation line to the left atrial appendage, or ablation of a complex fractionated atrial electrogram, etc.

By this method, an atrial arrhythmia, such as atrial fibrillation, can be successfully treated using a completely thoracoscopic method to produce a set of lesions chosen from among a group of Cox maze III set of lesions as disclosed above. Using the methods of the subject invention, an epicardial Cox maze III ablation procedure can be successfully completed on a beating heart, without the need to place the patient on cardio-pulmonary bypass. In addition, the methods can include thoracoscopically producing a lesion in the ganglionic plexi. Successful ablation can be verified with intraoperative electrophysiologic testing.

In some embodiments, a combination ablation and sensing device such as the Isolator® Multifunctional Pen (Atricure, Inc., Cincinnati, Ohio) can employed to evaluate the heart prior to production of the maze. The sensing portion of the device can be used to sense the pulmonary veins, to create a baseline map of the right pulmonary vein potentials. Additionally, in some embodiments, the methods can also include sensing in order to localize the ganglionic plexi. Autonomic ganglionic plexi (GP) are collections of nerves located on the surface of the heart. Autonomic GP can promote pulmonary vein arrhythmogenicity and facilitate induction of sustained atrial fibrillation by premature atrial depolarizations. The autonomic GP can therefore function as regulators of both pulmonary vein- and non-pulmonary vein-dependent mechanisms of atrial fibrillation. The GP can be mapped with high-frequency stimulation (e.g., at a rate of 800-1,000 impulses per minute), at a voltage (e.g., 18 volts) using any suitable sensing device. When the GP are stimulated they release acetylcholine, a neurotransmitter which is a potent blocker of the atrioventricular node (AV) node, the area of specialized tissue between the atria and the ventricles of the heart which conducts the normal electrical impulse from the atria to the ventricles. Acetylcholine can also slow down the sinoatrial node (SA node or sinus node) as well, which is the impulse-generating (pacemaker) tissue located in the right atrium of the heart, and thus the generator of sinus rhythm.

Release of acetylcholine by a stimulated GP can result in a significant decrease in heart rate (a bradycardic response). If a significant bradycardic response is seen (e.g., an increase in R-R of 50% or greater) after stimulation of a GP, this confirms the presence of an active GP which can be focally ablated. If there is no response when an area of tissue is stimulated (e.g., no significant increase in the R-R interval during stimulation) the stimulating device can be moved, and another area can be tested.

In some instances, a stimulating device, such as the pen disclosed above, can be placed in a location where a ganglionic plexus is known to be located, and then the ablating agent can be activated (e.g., radiofrequency energy), and the ganglionic plexus can be focally ablated. One or more ganglionic plexi can be ablated from the epicardial approach, using the devices as disclosed above. The methods can include repeating the ablating steps if necessary one or more times until it is determined that the GP has been ablated (e.g. no significant increase in the R-R interval is seen during stimulation). Further details of techniques of GP mapping and ablation that can be adapted for use with the subject methods are disclosed, for example, in the publication by Mehall, et al., entitled "Intraoperative Epicardial Electrophysiologic Mapping and Isolation of Autonomic Ganglionic Plexi". Therefore, in some embodiments, the methods can include thoracoscopically producing a lesion in a ganglionic plexus. After this step, the above sensing steps can be repeated to confirm conduction block post-ablation, discussed further below. The evaluation of ablation can be performed with the Isolator® Multifunctional Pen, or any other device suitable for thoracoscopic procedures that performs a similar function. The stimulating and sensing device can then be removed.

The subject methods find use in treating a cardiac arrhythmia, such as atrial fibrillation, by the epicardial ablation of cardiac tissue through openings in a subject's body using thoracoscopic methods. Although the Cox maze III set of lesions can be used for the treatment of AF, the methods of the subject invention can also be used to treat multiple cardiac arrhythmias, including but not limited to: all types of atrial fibrillation, including paroxysmal, persistent, long-standing persistent, and permanent AF, atrial flutter; atrioventricular (AV) node reentrant tachycardias; and atrioventricular (AV) reentry tachycardia (such as Wolff-Parkinson-White syndrome), and therefore any appropriate cardiac arrhythmia may be treated as described herein. Furthermore, the methods of the subject invention may also be used in combination with other thoracoscopic procedures. Although the methods as described above are directed to creation of a Cox maze III set of lesions in the atria, the methods of thoracoscopically producing a set of lesions can also be used to treat ventricular arrhythmias.

The subject methods also include the step of diagnosing a patient in need of surgical treatment for a cardiac arrhythmia, e.g., atrial fibrillation. Patients who need surgical treatment for an arrhythmia can include, for example, patients who cannot be anticoagulated, or patients who have failed medical therapy, or who cannot tolerate the side effects of anti-arrhythmic drugs.

Cardiac arrhythmias can have many different causes. For example, atrial fibrillation can have both cardiovascular causes (such as hypertensive heart disease, coronary artery disease, valvular heart disease, cardiomyopathies) and non-cardiovascular causes (such as lung disease, obesity, sleep apnea, metabolic disorders, toxins).

Therefore, the signs and symptoms associated with a cardiac arrhythmia will vary depending on the arrhythmia, and upon any associated condition. Signs and symptoms can include abnormal awareness of the heartbeat, or palpitations, lightheadedness or dizziness, shortness of breath, decreased exercise tolerance, fatigue, fainting. Some arrhythmias can result in cardiac failure, cardiac arrest, or sudden death. Some forms of arrhythmia may not cause symptoms, but can increase the risk of stroke. For example, patients with atrial fibrillation have an increased risk of embolism, transient ischemic attacks (TIAs), and stroke. Cardiac arrhythmias are often first detected by an abnormal peripheral pulse, or by auscultation of the heart with a stethoscope. These methods may not be sufficient to diagnose specific arrhythmias, but can give a general indication of the heart rate and whether it is regular or irregular.

Diagnostic tests can include physical examination, electrocardiogram (EKG; ECG); a Holter monitor, which is an EKG recorded over a 24-hour period to detect arrhythmias that may happen briefly and unpredictably throughout the day, imaging studies such as chest x-ray, ultrasound, computerized tomography (CT), magnetic resonance imaging (MRI), nuclear medicine studies such as a nuclear myocardial stress test, for example. Additionally, invasive studies including cardiac catheterization with electrophysiologic studies may be performed.

Treatment for arrhythmias, including AF, can include anti-arrhythmic drugs to prevent or control arrhythmias, and maintain the normal sinus rhythm of the heart. Medication to prevent clotting is also indicated in patients who are at risk for clots and emboli, which are clots which travel elsewhere in the body and can cause strokes, for example. Invasive treatments can include catheter ablation or modification of the atrioventricular (AV) node, with concomitant pacing of the heart, and catheter or surgical ablation procedures, such as the Cox maze III procedure.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Aspects of these embodiments of the invention are further described in terms of the following clauses.

1. A method of treating a subject for a cardiac arrhythmia, the method comprising thoracoscopically producing from the left-side of a subject a Cox maze III set of lesions in a manner sufficient to treat the subject for the cardiac arrhythmia, wherein at least a portion of the set of lesions is produced using a multipolar articulating ablation device.
2. The method according to Clause 1, wherein the Cox maze III set of lesions comprises a right pulmonary vein encircling ablation line, a left pulmonary vein encircling ablation line, a superior connecting ablation line connecting the right and left pulmonary vein encircling lines, and an inferior connecting ablation line connecting the right and left pulmonary vein encircling lines.
3. The method according to Clause 2, wherein the Cox maze III set of lesions further comprises an ablation line connecting the superior connecting ablation line to the base of the left atrial appendage.
4. The method according to Clause 2, wherein the Cox maze III set of lesions further comprises a left atrial appendectomy.
5. The method according to Clause 2, wherein the Cox maze III set of lesions further comprises an ablation line connecting the superior connecting ablation line to the fibrous trigone.
6. The method according to Clause 2, wherein the Cox maze III set of lesions further comprises an ablation line extending from the inferior connecting ablation line to the coronary sinus.
7. The method according to Clause 2, wherein the Cox maze III set of lesions further comprises an ablation line in the posterolateral wall of the right atrium connecting the superior vena cava to the inferior vena cava.
8. The method according to Clause 2, wherein the Cox maze III set of lesions further comprises an ablation line from the right pulmonary vein encircling ablation line to the posterolateral wall of the right atrium.
9. The method according to Clause 1, wherein the multipolar articulating ablation device is a quadripolar articulating linear combination ablation and a sensing device.
10. The method according to Clause 1, wherein the method further comprises dissecting the confluent tissue between the superior vena cava, left atrium and right pulmonary artery.
11. The method according to Clause 10, wherein the dissecting is performed with an endoscopic dissector rod with an atraumatic conical tip.
12. The method according to Clause 1, wherein the method further comprises amputating the left atrial appendage.
13. The method according to Clause 12, wherein the left atrial appendage is amputated using an integrated endoscopic occlusion amputation device.
14. The method according to Clause 1, wherein the method comprises ablating the atrial tissue surrounding the pulmonary veins using a multipolar atrial clamp.
15. The method according to Clause 14, wherein the multipolar atrial clamp is a quadripolar atrial clamp.
16. A linear multipolar articulating ablation sensing device comprising:
   a proximal end handle;
   a shaft; and
   a distal end linear multipolar articulating ablation sensing element.
17. A multipolar clamping device comprising:
   a proximal end handle;
   a shaft; and
   a distal end multipolar clamping element comprising first and second multipolar ablation jaws.
18. A multipolar curvilinear device comprising:
   a proximal end handle;
   a shaft; and
   a distal end flexible multipolar ablation element.
19. An endoscopic dissector rod with an atraumatic conical tip and hydrophilic coating.
20. An integrated endoscopic occlusion amputation device comprising a distal end integrated cutter/stapler and clip.
21. A kit for use in a method according to any of Clauses 1 to 15, wherein the kit comprises one or more of: a linear multipolar articulating ablation sensing device; a multipolar clamping device; an endoscopic dissector rod with an atraumatic conical tip and an integrated endoscopic occlusion amputation device.
22. The kit according to Clause 21, wherein the kit comprises two or more of: a linear multipolar articulating ablation sensing device; a multipolar clamping device; an endoscopic dissector rod with an atraumatic conical tip and an integrated endoscopic occlusion amputation device.
23. The kit according to Clause 21, wherein the kit comprises three or more of: a linear multipolar articulating ablation sensing device; a multipolar clamping device; an endoscopic dissector rod with an atraumatic conical tip and an integrated endoscopic occlusion amputation device.
24. The kit according to Clause 21, wherein the kit comprises all of: a linear multipolar articulating ablation sensing device; a multipolar clamping device; an endoscopic dissector rod with an atraumatic conical tip and an integrated endoscopic occlusion amputation device.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A tissue ablation device, the device comprising:
    an elongated member having a proximal and distal end;
    first and second jaws at or near the distal end, with at least one of the first and second jaws being collapsible into the elongated member, wherein the first and second jaws are configured to apply intra and inter ablation energy to tissue disposed between the jaws during use, with the first jaw having a central elongated electrode comprising a plurality of positive temperature co-efficient of resistivity (PTCR) material ablation elements connected in series wherein said plurality is flanked by two non-PTCR material electrodes, and with the second jaw having a central elongated electrode comprising a second plurality of PTCR material ablation elements connected in series wherein said second plurality is flanked by two additional non-PTCR material electrodes; and
    a connector at the proximal end for operatively connecting to an ablation energy source.

2. The tissue ablation device according to claim 1, wherein one or more of the PTCR material ablation elements comprises a semiconducting titanate ceramic.

3. The tissue ablation device according to claim 1, wherein the first and second jaws are configured to not exceed a predetermined compressive force limit on tissue positioned between the jaws during use.

4. The tissue ablation device according to claim 1, wherein the first and second jaws are configured to assume a parallel configuration prior to clamping tissue.

5. The tissue ablation device according to claim 1, wherein at least one of the first and second jaws comprises an illumination element.

6. A method of ablating tissue, the method comprising:
    positioning the tissue between first and second jaws of a tissue ablation device according to claim 1, wherein the tissue ablation device is operatively coupled to an ablation energy source; and
    applying intra and inter ablation energy to the tissue disposed between the first and second jaws to ablate the tissue.

7. The method according to claim 6, wherein the tissue is part of a living animal.

8. The method according to claim 7, wherein the tissue is cardiac tissue.

9. The method according to claim 6, wherein the method is an open surgical procedure.

10. The method according to claim 6, wherein the method is a minimally invasive surgical procedure.

11. The method according to claim 6, wherein at least one of the first and second jaws comprises an illumination element and the method further comprises detecting light from the illumination element with a detector.

12. A kit comprising: a tissue ablation device according to claim 1; and sterile packaging, wherein the tissue ablation device is present in the sterile packaging.

13. A system for ablating cardiac tissue, comprising:
    a tissue ablation device with an elongated member having a proximal and distal end;
    first and second jaws at or near the distal end, with at least one of the first and second jaws being collapsible into the elongated member, wherein the first and second jaws are configured to apply intra and inter ablation energy to tissue disposed between the jaws during use, with the first jaw having a central elongated electrode comprising a plurality of positive temperature co-efficient of resistivity (PTCR) material ablation elements connected in series element that wherein said plurality is flanked by two non-PTCR material electrodes, and with the second jaw having a central elongated electrode comprising a second plurality of PTCR material ablation elements connected in series wherein said second plurality is flanked by two additional non-PTCR material electrodes; and
    a connector at the proximal end for operatively connecting to an ablation energy source.

* * * * *